United States Patent
Her et al.

(10) Patent No.: US 11,780,922 B2
(45) Date of Patent: *Oct. 10, 2023

(54) BIFUNCTIONAL PROTEINS COMBINING CHECKPOINT BLOCKADE FOR TARGETED THERAPY

(71) Applicant: AP Biosciences, Inc., Taipei (TW)

(72) Inventors: Jeng-Horng Her, San Jose, CA (US); Jhong-Jhe You, Taipei (TW); Ching-Hsuan Hsu, Taoyuan (TW); Po-Lin Huang, Taipei (TW)

(73) Assignee: AP Biosciences, Inc., Taipei (TW)

( * ) Notice: Subject to any disclaimer, the term of this patent is extended or adjusted under 35 U.S.C. 154(b) by 235 days.

This patent is subject to a terminal disclaimer.

(21) Appl. No.: 16/896,597

(22) Filed: Jun. 9, 2020

(65) Prior Publication Data

US 2020/0299389 A1 Sep. 24, 2020

Related U.S. Application Data

(63) Continuation-in-part of application No. PCT/US2019/019786, filed on Feb. 27, 2019.

(60) Provisional application No. 62/636,825, filed on Feb. 28, 2018.

(51) Int. Cl.
| | | |
|---|---|---|
| C07K 16/00 | (2006.01) | |
| C07K 16/28 | (2006.01) | |
| A61K 47/68 | (2017.01) | |
| A61P 35/00 | (2006.01) | |
| C07K 14/71 | (2006.01) | |
| G01N 33/574 | (2006.01) | |
| C07K 14/72 | (2006.01) | |
| A61K 39/00 | (2006.01) | |

(52) U.S. Cl.
CPC ...... C07K 16/2827 (2013.01); A61K 47/6803 (2017.08); A61P 35/00 (2018.01); C07K 14/71 (2013.01); C07K 14/723 (2013.01); G01N 33/574 (2013.01); A61K 2039/505 (2013.01); C07K 2317/21 (2013.01); C07K 2317/31 (2013.01); C07K 2317/52 (2013.01); C07K 2317/55 (2013.01); C07K 2317/732 (2013.01); C07K 2317/76 (2013.01)

(58) Field of Classification Search
CPC .......... A61K 47/6803; A61K 2039/505; A61P 35/00; G01N 33/574; C07K 2317/52; C07K 2317/732; C07K 2319/00
See application file for complete search history.

(56) References Cited

U.S. PATENT DOCUMENTS

| | | |
|---|---|---|
| 9,527,901 B2 | 12/2016 | Jing |
| 9,567,403 B2 | 2/2017 | Wu et al. |
| 9,895,441 B2 | 2/2018 | Maecker et al. |
| 9,987,500 B2 | 6/2018 | Papadopoulos et al. |
| 10,273,311 B2 | 4/2019 | Desir |
| 10,301,395 B2 | 5/2019 | Fu et al. |
| 2008/0254512 A1 | 10/2008 | Capon |
| 2014/0154253 A1 | 6/2014 | Ng et al. |
| 2014/0213769 A1 | 7/2014 | Hong et al. |
| 2014/0294837 A1 | 10/2014 | Song et al. |
| 2015/0044216 A1* | 2/2015 | Wu .......... A61P 35/00 435/328 |
| 2015/0202291 A1 | 7/2015 | Bosch et al. |
| 2016/0122829 A1 | 5/2016 | Hammerman |
| 2016/0159905 A1 | 6/2016 | Abdiche et al. |
| 2017/0137539 A1 | 5/2017 | Fu et al. |
| 2017/0275362 A1 | 9/2017 | Brentjens et al. |
| 2017/0281765 A1 | 10/2017 | Zhou et al. |
| 2017/0283488 A1 | 10/2017 | Yu et al. |
| 2017/0369552 A1* | 12/2017 | Zen .......... A61P 27/02 |
| 2018/0346573 A1 | 12/2018 | Fang et al. |
| 2019/0008956 A1 | 1/2019 | Chaplin et al. |
| 2019/0038734 A1 | 2/2019 | Wallin et al. |
| 2019/0091331 A1 | 3/2019 | Yang et al. |

FOREIGN PATENT DOCUMENTS

| | | |
|---|---|---|
| CN | 107207593 A | 9/2017 |
| CN | 107602702 A | 1/2018 |
| JP | 2016540042 A | 12/2016 |
| RU | 2689760 C2 | 5/2019 |
| WO | 2015018306 A1 | 2/2015 |
| WO | 2015112800 A1 | 7/2015 |
| WO | 2015148416 A1 | 10/2015 |
| WO | 2015200790 A2 | 12/2015 |
| WO | 2017031157 A1 | 2/2017 |
| WO | 2017087603 A1 | 5/2017 |
| WO | 2017136562 A2 | 8/2017 |
| WO | 2017181079 A2 | 10/2017 |

(Continued)

OTHER PUBLICATIONS

Qian et al (Protein Expression and Purification 109:1-6 2015 (Year: 2015).*
Tecentriq (atezolizumab), US Food and Drug Administration, 2016, pp. 1-38, San Francisco.
Atezolizumab, Wikipedia, retrieved from https://en.wikipedia.org/wiki/Atezolizumab accessed on May 4, 2021, pp. 1-10.
Liang, Optimising first-line treatment for metastatic renal cell carcinoma, Correspondence, 2020, vol. 395:10219, Abstract, pp. e7-e13, Spain.

(Continued)

Primary Examiner — Lei Yao
(74) Attorney, Agent, or Firm — THE WEBB LAW FIRM

(57) ABSTRACT

Provided are bispecific proteins that comprise a binding domain binding cell surface protein and a vascular endothelial growth factor (VEGF) inhibiting domain. Provided also is an antibody-drug conjugate that comprises a therapeutic agent and an antibody or an antigen-binding fragment binding PD-L1 and/or a VEGF inhibiting domain, wherein the therapeutic agent is covalently conjugated to the antibody or the antigen-binding fragment by a linker.

15 Claims, 19 Drawing Sheets

Specification includes a Sequence Listing.

(56) References Cited

FOREIGN PATENT DOCUMENTS

| WO | 2017200173 | A1 |   | 11/2017 |
| WO | 2017215590 | A1 |   | 12/2017 |
| WO | 2019062642 | A1 |   | 4/2019 |
| WO | WO2019062642 | | * | 4/2019 |
| WO | WO2019133817 | | * | 4/2019 |

OTHER PUBLICATIONS

Lee et al., "Multi-paratopic VEGF decoy receptor have superior anti-tumor effects through anti-EGFRs and targeted anti-angiogenic activities", Biomaterials, 2018, pp. 34-45. vol. 171.

Bargou et al., "Tumor Regression in Cancer Patients by Very Low Doses of a T Cell-Engaging Antibody", Science, 2008, pp. 974-977, vol. 321, No. 5891.

Bretscher et al., "A Theory of Self-Nonself Discrimination", Science, 1970, pp. 1042-1049, vol. 169, No. 3950.

Bretscher, "A two-step, two-signal model for the primary activation of precursor helper T cells", Proceedings of the National Academy of Sciences of the United States of America, 1999, pp. 185-190, vol. 96, No. 1.

Chames et al., "Bispecific antibodies for cancer therapy: The light at the end of the tunnel?", mAbs, 2009, pp. 539-547, vol. 1, No. 6.

Chen et al., "Elements of cancer immunity and the cancer-immune set point", Nature, 2017, pp. 321-330, vol. 541, No. 7637.

Demarest et al., "Antibody therapeutics, antibody engineering, and the merits of protein stability", Current Opinion in Drug Discovery & Development, 2008, pp. 675-687, vol. 11, No. 5.

Ferrara et al., "Bevacizumab (Avastin), a humanized anti-VEGF monoclonal antibody for cancer therapy", Biochemical and Biophysical Research Communications, 2005, pp. 328-335, vol. 333, No. 2.

Fridman et al., "The immune contexture in human tumours: impact on clinical outcome", Nature Reviews Cancer, 2012, pp. 298-306, vol. 12, No. 4.

Goldenberg et al., "Cancer imaging and therapy with bispecific antibody pretargeting", Update on Cancer Therapeutics, 2007, pp. 19-31, vol. 2, No. 1.

Heiss et al., "The trifunctional antibody catumaxomab for the treatment of malignant ascites due to epithelial cancer: results of a prospective randomized phase II/III trial", International Journal of Cancer, 2010, pp. 2209-2221, vol. 127, No. 9.

Hicklin et al., "Role of the Vascular Endothelial Growth Factor Pathway in Tumor Growth and Angiogenesis", Journal of Clinical Oncology, 2005, pp. 1011-1027, vol. 23, No. 5.

Holash et al., "VEGF-Trap: A VEGF blocker with potent antitumor effects", Proceedings of the National Academy of Sciences of the United States of America, 2002, pp. 11393-11398, vol. 99, No. 17.

Hollander, "Bispecific antibodies for cancer therapy", Immunotherapy, 2009, pp. 211-222, vol. 1, No. 2.

Hughes et al., "Targeted Therapy and Checkpoint Immunotherapy Combinations for the Treatment of Cancer", Trends in Immunology, 2016, pp. 462-476, vol. 37, No. 7.

Jenkins et al., "Antigen Presentation by Chemically Modified Splenocytes Induces Antigen-Specific T Cell Unresponsiveness in vitro and in vivo", The Journal of Experimental Medicine, 1987, pp. 302-319, vol. 165, No. 2.

Karpovsky et al., "Production of Target-Specific Effector Cells Using Hetero-cross-linked Aggregates Containing Anti-target Cell and Anti-Fcγ Receptor Antibodies", The Journal of Experimental Medicine, 1984, pp. 1686-1701, vol. 160, No. 6.

Kim et al., "Immune escape to PD-L1/PD-1 blockade: seven steps to success (or failure)", Annals of Oncology, 2016, pp. 1492-1504, vol. 27, No. 8.

King et al., "A new Hu-PBL model for the study of human islet alloreactivity based on NOD-scid mice bearing a targeted mutation in the IL-2 receptor gamma chain gene", Clinical Immunology, 2008, pp. 303-314, vol. 126, No. 3.

Koh et al., "PD-L1 expression correlates with VEGF and microvessel density in patients with uniformly treated classical Hodgkin lymphoma", Annals of Hematology, 2017, pp. 1883-1890, vol. 96, No. 11.

Lafferty et al., "A New Analysis of Allogeneic Interactions", The Australian Journal of Experimental Biology and Medical Science, 1975, pp. 27-42, vol. 53, Part 1.

Larkin et al., "Combined Nivolumab and Ipilimumab or Monotherapy in Untreated Melanoma", The New England Journal of Medicine, 2015, pp. 23-34, vol. 373, No. 1.

Lenschow et al., "CD28/B7 System of T cell Costimulation", Annual Review of Immunology, 1996, pp. 233-258, vol. 14.

Liang et al., "PD-L1 and PD-L2 have distinct roles in regulating host immunity to cutaneous leishmaniasis", European Journal of Immunology, 2006, pp. 58-64, vol. 36, No. 1.

Lu et al., "A Fully Human Recombinant IgG-like Bispecific Antibody to Both the Epidermal Growth Factor Receptor and the Insulin-like Growth Factor Receptor for Enhanced Antitumor Activity", The Journal of Biological Chemistry, 2005, pp. 19665-19672, vol. 280, No. 20.

Müller et al., "Improved Pharmacokinetics of Recombinant Bispecific Antibody Molecules by Fusion to Human Serum Albumin", The Journal of Biological Chemistry, 2007, pp. 12650-12660, vol. 282, No. 17.

Pardoll, "The blockade of immune checkpoints in cancer immunotherapy", Nature Review Cancer, 2012, pp. 252-264, vol. 12, No. 4.

Perez et al., "Specific targeting of cytotoxic T cells by anti-T3 linked to anti-target cell antibody", Nature, 1985, pp. 354-356, vol. 316, No. 6026.

Poon et al., "Serum Vascular Endothelial Growth Factor Predicts Venous Invasion in Hepatocellular Carcinoma: A Prospective Study", Annals of Surgery, 2001, pp. 227-235, vol. 233, No. 2.

Ridgway et al., "'Knobs-into-holes' engineering of antibody CH3 domains for heavy chain heterodimerization", Protein Engineering, 1996, pp. 617-621, vol. 9, No. 7.

Roskoski Jr., "Sunitinib: A VEGF and PDGF receptor protein kinase and angiogenesis inhibitor", Biochemical and Biophysical Research Communications, 2007, pp. 323-328, vol. 356, No. 2.

Sedykh et al., "Bispecific antibodies: design, therapy, perspectives", Drug Design, Development and Therapy, 2018, pp. 195-208, vol. 12.

Staerz et al., "Hybrid antibodies can target sites for attack by T cells", Nature, 1985, pp. 628-631, vol. 314, No. 6012.

Stewart, "Aflibercept (VEGF-TRAP): The Next Anti-VEGF Drug", Inflammation & Allergy—Drug Targets, 2011, pp. 497-508, vol. 10.

Sznol et al., "Antagonist Antibodies to PD-1 and B7-H1 (PD-L1) in the Treatment of Advanced Human Cancer," Clinical Cancer Research, 2013, pp. 1021-1034, vol. 19, No. 5.

Terme et al., "Modulation of Immunity by Antiangiogenic Molecules in Cancer", Clinical and Developmental Immunology, 2012, 8 pages, vol. 2012, Article ID. 492920.

Thakur et al., "Cancer therapy with bispecific antibodies: Clinical experience", Current Opinion in Molecular Therapeutics, 2010, pp. 340-349, vol. 12, No. 3.

Topalian et al., "Survival, Durable Tumor Remission, and Long-Term Safety in Patients With Advanced Melanoma Receiving Nivolumab", Journal of Clinical Oncology, 2014, pp. 1020-1030, vol. 32, No. 10.

Xue et al., "Relationship between expression of PD-L1 and tumor angiogenesis, proliferation, and invasion in glioma", Oncotarget, 2017, pp. 49702-49712, vol. 8, No. 30.

Wallin et al., "Atezolizumab in combination with bevacizumab enhances antigen-specific T-cell migration in metastatic renal cell carcinoma", Nature Communications, 2016, 8 pages, vol. 7, Article No. 12624.

Lu et al., "Abstract 572: A novel anti-PDL1 x anti-VEGFR2 bispecific antibody for enhanced antitumor immunity," Cancer Research, Jul. 2016, p. 572, 76 (14 Supplement).

Alessi et al., "PD-1/PD-L1 and VEGF-A/VEGF-C expression in lymph node microenvironment and association with melanoma metastasis and survival", Melanoma Research, 2017, pp. 565-572, vol. 27:6.

(56) References Cited

OTHER PUBLICATIONS

Carter et al., "Next generation antibody drugs: pursuit of the 'high-hanging fruit'", Nature Reviews, Mar. 2018, pp. 197-223, vol. 17.

Hoseini et al., "Acute myeloid leukemia targets for bispecific antibodies", Blood Cancer Journal, 2017, pp. 1-12, vol. 7.

* cited by examiner

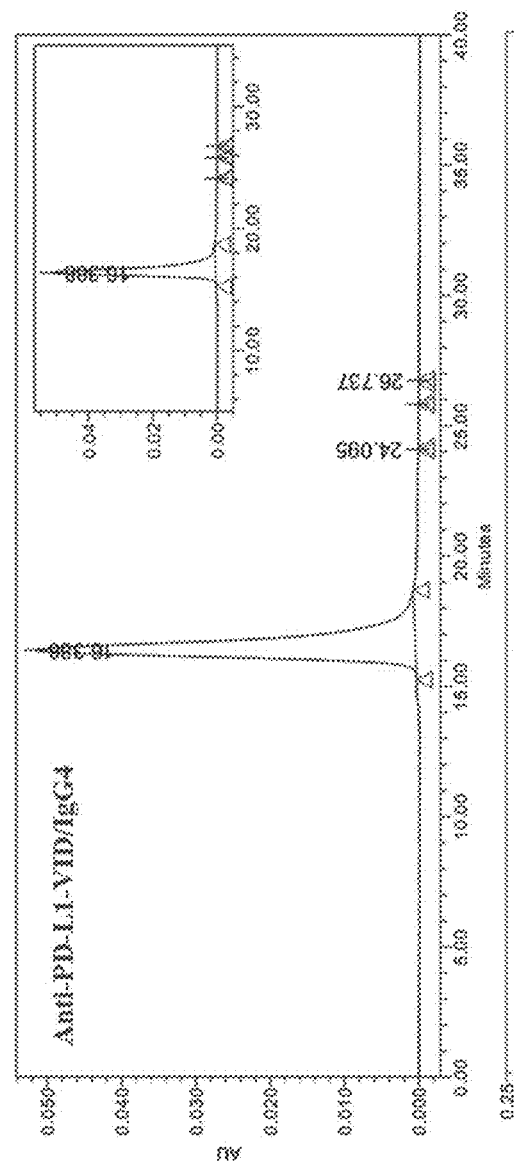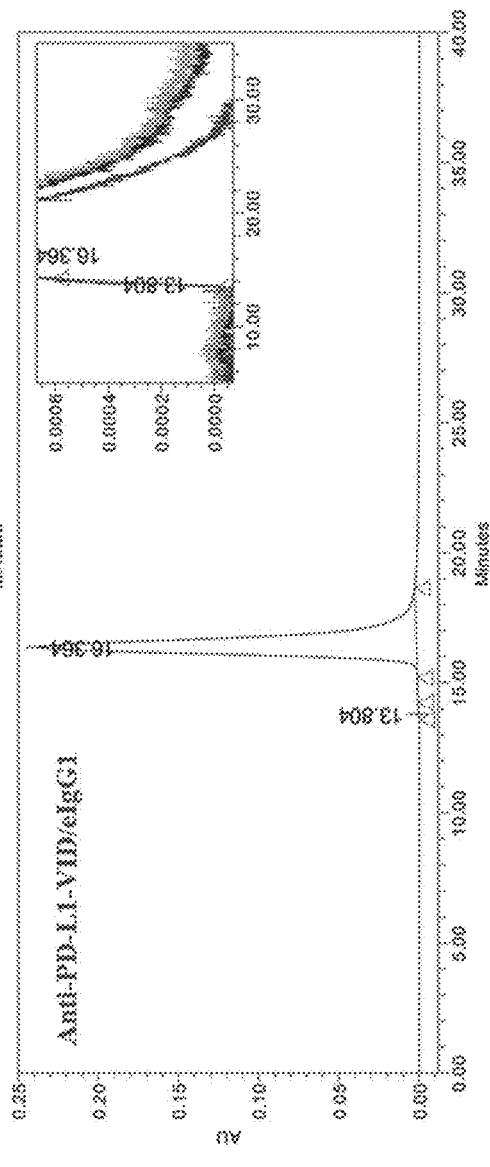

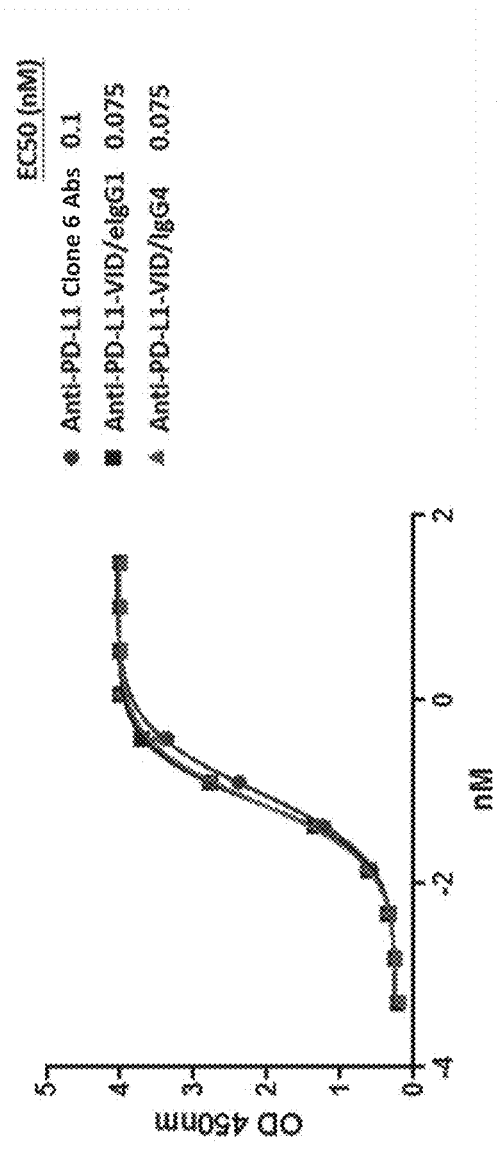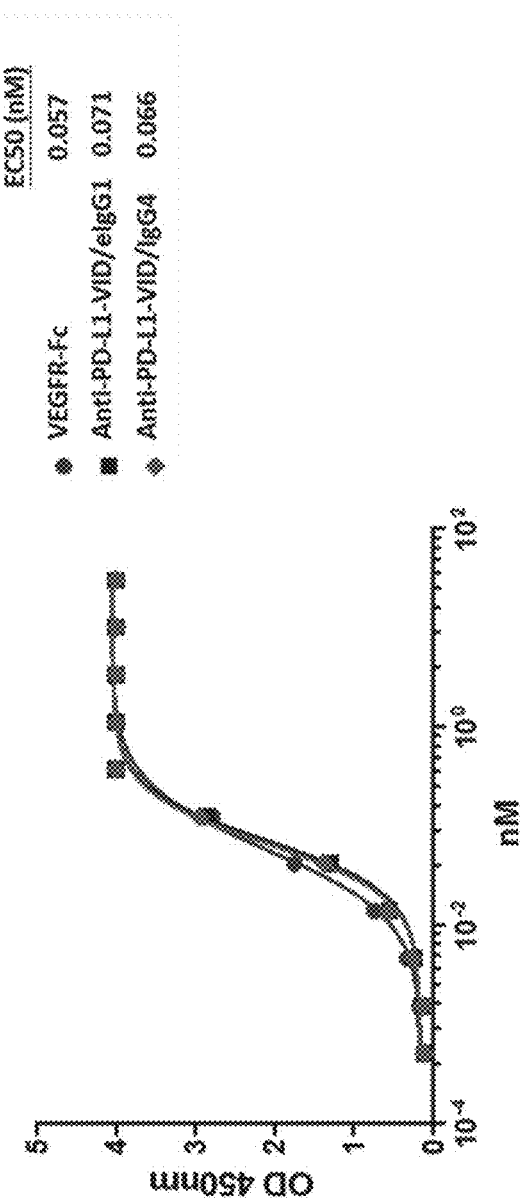
Fig. 11A
Fig. 11B

BIFUNCTIONAL PROTEINS COMBINING CHECKPOINT BLOCKADE FOR TARGETED THERAPY

CROSS-REFERENCE TO RELATED APPLICATIONS

This application is a Continuation-in-part of International application No. PCT/US2019/019786 filed Feb. 27, 2019 and claims priority to U.S. Provisional Patent Application No. 62/636,825 filed Feb. 28, 2018, the disclosures of which are hereby incorporated by reference in their entirety.

The Sequence Listing contained in the electronic file titled "2003117_ST25" created Jun. 4, 2020, comprising 547 MB, is hereby incorporated herein.

BACKGROUND OF THE INVENTION

Field of Invention

The present invention relates to an antibody. More particularly, the present invention relates to the antibody for cancer therapy.

Description of Related Art

The two major types of lymphocytes in humans are T (thymus-derived) and B (bone marrow derived). These cells are derived from hematopoietic stem cells in the bone marrow and fetal liver that have committed to the lymphoid development pathway. The progeny of these stem cells follow divergent pathways to mature into either B or T lymphocytes. Human B-lymphocyte development takes place entirely within the bone marrow. T cells, on the other hand, develop from immature precursors that leave the marrow and travel through the bloodstream to the thymus, where they proliferate and differentiate into mature T lymphocytes.

T Cells

T-cells are the most abundant (about 75% of blood lymphocytes) and potent immune killer cells. The role of effector T-cells in the anti-tumor immune response is strongly supported by in vitro studies and the observation that a high infiltration of $CD8^+$ T cells in several types of tumors correlates with a favorable clinical prognostic (Fridman et al., 2012). The activation of effector naive T-cells requires at least three complementary signals: (i) TCR-CD3/Ag-MHC interaction with the assistance of co-receptors (CD4 or CD8); (ii) binding of co-stimulatory molecules such as CD80 or CD86 to CD28, CD40/CD40L; and (iii) accessory molecules such as cytokines.

Co-stimulation or the provision of two distinct signals to T-cells is a widely accepted model of lymphocyte activation of resting T lymphocytes by antigen-presenting cells (APCs) (Lafferty and Cunningham, 1975). This model further provides for the discrimination of self from non-self and immune tolerance (Bretscher and Cohn, 1970; Bretscher, 1999; Jenkins and Schwartz, 1987). The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs), and induce T-cells to promote clonal expansion, cytokine secretion and effector function (Lenschow et al., 1996). In the absence of costimulation, T-cells can become refractory to antigen stimulation, do not mount an effective immune response, and further may result in exhaustion or tolerance to foreign antigens.

Immune Checkpoint Protein: PD-L1

Immune checkpoints refer to a group of inhibitory and stimulatory pathways mostly initiated by ligand-receptor interaction hardwiring the immune system, specifically T-cell mediated immunity, to maintain self-tolerance and modulate the duration and amplitude of physiological responses in peripheral tissues in order to minimize collateral tissue damages normally (Pardoll, 2012). Tumor cells co-opt certain checkpoint pathways as a major mechanism of immune resistance. For example, programmed cell death protein 1 ligand, PD-L1, is commonly up-regulated on tumor cell surface of human cancers. The interaction of PD-L1 with its receptor, PD-1, expressed on tumor infiltrated lymphocytes (TILs), specifically on T cells, inhibits local T cell-mediated response to escape the immune surveillance (Liang et al., 2006; Sznol and Chen, 2013). Thus, the inhibition of immunosuppressive signals on cancer cells, or direct agonistic stimulation of T cells, results in and/or induces a strong sustained anti-tumor immune response. Recent clinical studies strongly suggested blockage of immune checkpoint proteins via antibody or modulated by soluble ligands or receptors are the most promising approaches to activating therapeutic antitumor immunity (Topalian et al., 2014). Currently, anti-PD-1 and anti-CTLA-4 (cytotoxic T-lymphocyte-associated antigen-4) antibodies have been approved by FDA to treat diseases such as melanomas.

Angiogenesis and VEGF Inhibition Domain (VID)

Angiogenesis, the formation of new blood vessels from pre-existing blood vessels, is a normal and vital process involved in fetal development and tissue repair. The process is highly regulated by both angiogenic and anti-angiogenic factors, and it involves endothelial cell migration and proliferation, vessel maturation and remodeling, and degradation of the extracellular matrix. Although it is an important process in normal growth and development, angiogenesis also plays a key role in tumor growth. Tumors require a vascular supply to grow and can achieve this via the expression of pro-angiogenic growth factors, including members of the vascular endothelial growth factor (VEGF) family of ligands (Hicklin and Ellis, 2005). When VEGF and other endothelial growth factors bind to their receptors on endothelial cells, signals within these cells are initiated that promote the growth and survival of new blood vessels. Blocking VEGF activity with VEGF specific antibody (Avastin), soluble VEGF receptors (aflibercept), or inhibitors of VEGF tyrosine kinase activity (sunitinib) are strategies that have been used to treat tumor or angiogenic-type disorders, such as AMD.

Bi-Specific/Bi-Functional Antibody

The idea of using bispecific antibodies to efficiently retarget effector immune cells toward tumor cells emerged in the 1980s (Karpovsky et al., 1984; Perez et al., 1985; Staerz et al., 1985). Bispecific scaffolds are generally classified in two major groups with different pharmacokinetic properties, based on the absence or presence of an Fc fragment, IgG-like molecules and small recombinant bispecific formats, most of them deriving from single chain variable fragment (scFv). Through their compact size, antibody fragments usually penetrate tumors more efficiently than IgG-like molecules but this benefit is mitigated by a short serum half-life (few hours) limiting their overall tumor uptake and residence time (Goldenberg et al., 2007). By contrast, the presence of an Fc fragment, which binds to the neonatal Fc receptors, provides a long serum half-life (>10 days) to the IgG-like formats, favoring tumor uptake and retention, but limits tumor penetration.

Recent studies have highlighted the therapeutic efficacy of immunotherapy, a class of cancer treatments that utilize the patient's own immune system to destroy cancerous cells. Within a tumor the presence of a family of negative regulatory molecules, collectively known as "checkpoint inhibitors," can inhibit T cell function to suppress anti-tumor immunity. Checkpoint inhibitors, such as CTLA-4 and PD-1, attenuate T cell proliferation and cytokine production. Targeted blockade of CTLA-4 or PD-1 with antagonist monoclonal antibodies (mAbs) releases the "brakes" on T cells to boost anti-tumor immunity. Also, recent studies have reported the associations between PD-L1 or PD-L2/PD-1 pathways and pro-angiogenic genes including hypoxia inducible factors (HIFs) and vascular endothelial growth factor (VEGF) in several malignancies, such as classical Hodgkin lymphoma (cHL) (Koh et al., 2017) and glioma (Xue et al., 2017). Koh et al. confirmed the positive correlations between PD-L1, VEGF, or MVD. Their findings provided evidence supporting new therapeutic approaches including combinations of anti-PD-L1/PD-1 and anti-VEGF therapy in addition to the current standard regimen for cHL (Koh et al., 2017). VEGF also evidenced its ability to disrupt a key step in the cancer immunity cycle: T-cell infiltration into the tumor (Kim and Chen, 2016; Terme et al., 2012). Targeting VEGF may help restore part of the cancer immunity cycle by increasing T-cell infiltration into the tumor microenvironment (Hughes et al., 2016; Terme et al., 2012; Wallin et al., 2016). VEGF pathway inhibition may lead to increased expression of cell adhesion molecules on endothelial cells, increasing intratumoral T cells to create an immune inflamed tumor microenvironment.

SUMMARY OF THE INVENTION

The present disclosure designed to investigate the bispecific antibody with immunomodulatory aiming and angiogenesis inhibition for the treatment of patient with cancers, such as prostate cancer, lung cancer, NSCLC, melanoma, lymphoma, breast cancer, head and neck cancer, RCC, or ovarian cancer were examined.

The present disclosure provides a bispecific antibody or antigen-binding portion thereof comprising at least one of polypeptide chain, wherein the polypeptide chain comprising: a binding domain binding cell surface protein; and a vascular endothelial growth factor (VEGF) inhibiting domain.

In one embodiment, the cell surface protein comprising programmed cell death protein 1 ligand (PD-L1), programmed cell death protein 1 (PD-1), epidermal growth factor receptor (EGFR), human epidermal growth factor receptor 2 (HER2), cytotoxic T-lymphocyte-associated antigen 4 (CTLA-4), lymphocyte activation gene 3 (LAG3), B- and T-lymphocyte attenuator (BTLA), OX40 (cluster of differentiation 134, CD134), CD27, CD28, tumor necrosis factor receptor superfamily member 9 (TNFRSF9 or CD137), inducible T cell costimulator (ICOS or CD278), CD40, or a combination thereof.

In one embodiment, the binding domain binds the PD-L1, and the binding domain comprises: a heavy chain variable domain comprising an amino acid sequence of at least about 80% sequence homology to the amino acid sequence selected from the group consisting of SEQ ID NO: 4 and 6; and a light chain variable domain comprising an amino acid sequence of at least about 80% sequence homology to the amino acid sequence selected from the group consisting of amino acid 1-111 of SEQ ID NO: 3 and 1-110 of SEQ ID NO: 5.

In one embodiment, the VEGF inhibiting domain is from human VEGF receptor 1 (VEGFR-1) or human VEGF receptor 2 (VEGFR-2).

In one embodiment, the VEGF inhibiting domain comprising an amino acid sequence of at least about 80% sequence homology to the amino acid sequence selected from the group consisting of SEQ ID NO: 1, 2, 9, 14, 15, 16, 17, 18, 19, 20, 21, 22, 23, 24, 25, 26, 27, and a combination thereof.

In one embodiment, the bispecific antibody or antigen-binding portion thereof further comprises: a Fc domain; and a Fab fragment connected to the N-terminus of the Fc domain, and the Fab fragment comprising the binding domain, wherein the VEGF inhibiting domain is connected to the C-terminus of the Fc domain.

In one embodiment, the bispecific antibody or antigen-binding portion thereof further comprises a linker between the Fc domain and the VEGF inhibiting domain.

In one embodiment, the bispecific antibody comprises an amino acid sequence set forth in SEQ ID NO: 12 or 13.

In one embodiment, the bispecific antibody or antigen-binding portion thereof comprises one pairs of polypeptide chains.

In one embodiment, the bispecific antibody is an IgG, IgE, IgM, IgD, IgA, or IgY antibody.

In one embodiment, the bispecific antibody is an IgG antibody.

In one embodiment, the IgG antibody is an IgG1, IgG2, IgG3, or IgG4 antibody.

In one embodiment, the IgG1 antibody is a reduction of antibody-dependent cell-mediated cytotoxity of IgG1 antibody.

In one embodiment, the bispecific antibody is a human antibody.

The present disclosure also provides a pharmaceutical composition, comprising: a bispecific antibody or an antigen-binding portion thereof as above mentioned, and at least one pharmaceutically acceptable carrier.

The present disclosure also provides an antibody-drug conjugate comprising: a therapeutic agent; and a bispecific antibody or an antigen-binding portion binding PD-L1 and/or a VEGF inhibiting domain, wherein the therapeutic agent is covalently conjugated to the antibody or the antigen-binding portion by a linker.

In one embodiment, the bispecific antibody or an antigen-binding portion is selected from the bispecific antibody or an antigen-binding portion as above mentioned.

The present disclosure also provides a method of treating cancer, the method comprising administering to the subject in need thereof an effective amount of the bi-specific antibody or antigen-binding portion as above mentioned.

In one embodiment, the cancer is selected from the group consisting of prostate cancer, lung cancer, Non-Small Cell Lung Cancer (NSCLC), melanoma, lymphoma, breast cancer, head and neck cancer, renal cell carcinoma (RCC), and ovarian cancer.

In one embodiment, the effective amount is from 0.001 µg/kg to 250 mg/kg.

The present disclosure also provides a nucleic acid molecule encoding the antibody or the antigen-binding portion as above mentioned.

The present disclosure also provides a method for cancer diagnosis in a subject, comprising: (a) obtaining a body fluid sample or a cell sample from a subject; (b) contacting the body fluid sample or the cell sample with one or more antibodies that can detect expression of a panel of cancer markers selected from the group consisting PD-L1 and VEGF; (c) assaying the binding of the one or more antibodies to the cell sample or the body fluid sample; and (d) assessing the cancer status of the subject in an assay by measuring and comparing the level of antibody binding with a normal control to determine the presence of the cancer in the subject.

The present disclosure also provides a method for assessing the risk of a subject suffering from cancer or a method for cancer screening in a subject, comprising: (a) obtaining a body fluid sample or a cell sample from a subject; (b) contacting the body fluid sample or the cell sample with one or more antibodies that can detect expression of a panel of cancer markers selected from the group consisting PD-L1 and VEGF; (c) assaying the binding of the one or more antibodies to the cell sample or the body fluid sample; and (d) assessing the cancer status of the subject in an assay by measuring and comparing the level of antibody binding with a normal control to determine whether the subject having the risk of suffering from cancer.

BRIEF DESCRIPTION OF THE DRAWINGS

The invention can be more fully understood by reading the following detailed description of the embodiment, with reference made to the accompanying drawings as follows:

FIGS. 10A and 10B show the purity of purified anti-PD-L1-VID/IgG4 (FIG. 10A) and anti-PD-L1-VID/eIgG1 (FIG. 10B) bispecific antibodies from HEK293 cells by SEC-HPLC analysis.

FIGS. 11A and 11B show examples of the PD-L1 (FIG. 11A) and $VEGF_{165}$ (FIG. 11B) binding activity of purified anti-PD-L1-VID bispecific antibodies by direct ELISA. Ligand pre-coated wells were first incubated with various concentrations of test samples as indicated. The bound Abs were then detected with HRP conjugated goat anti-human IgG Fc or F(ab')$_2$ specific antibody and $OD_{450}$ readings were plotted.

FIG. 14B: Mouse serum; FIG. 14C: Cyno serum). Purified antibody was incubated in serum (15 μg/mL) from different species as indicated at 37° C. for 1, 2, 3, 5, 7, and 14 days. After incubation, the collected samples were applied for sandwich ELISA assay to determine the relative binding activity for PD-L1 and $VEGF_{165}$. The half-life were plotted based on the concentration of bispecific antibody in serum.

DESCRIPTION OF THE INVENTION

Figure 1:
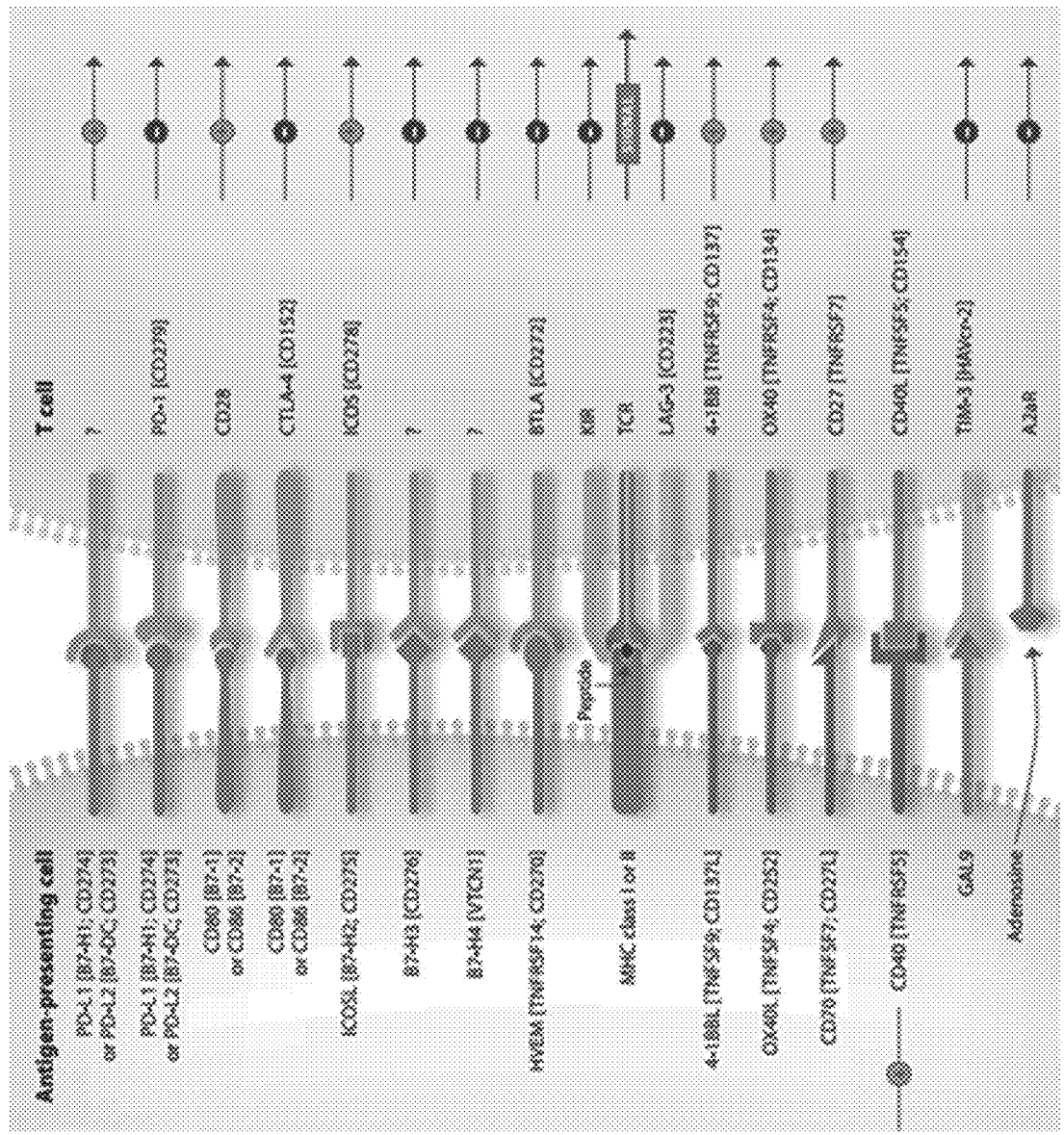
FIG. 1 shows immune checkpoints modulating T-cell mediated immunity. Antibody either agonistic or antagonistic against the checkpoints, such as anti-ICOS, anti-CD28, anti-OX40, and anti-CD27, or anti-PD-1, anti-CTLA4, anti-LAG3, anti-BTLA, could be used to construct the bi-functional fusion protein depending on applications.

Reference will now be made in detail to the present embodiments of the invention, examples of which are illustrated in the accompanying drawings. Wherever possible, the same reference numbers are used in the drawings and the description to refer to the same or like parts.

The present invention describes the expression, purification and characterization of bi-functional proteins with isolated functional VEGF inhibition domain to the C-terminal of Fc domain of anti-immune checkpoint protein antibodies. These proteins interact with its corresponding check point target shall transmit the inhibitory signal to modulate T-cell involved immunity and neutralized the VEGF-induced angiogenesis at the same time. The components of Fc fusion proteins in present invention are of all human origins, and thus are expected to be non-immunogenic and can be used as therapeutics in human.

Bispecific molecules such as bispecific antibodies (Bs-Abs) provide a means of simultaneously targeting multiple epitopes on the same molecular target or different targets with a single therapeutic agent. As cancer therapeutics, they have the potential to confer novel or more potent activities, lower the cost of goods and facilitate the development of new therapeutic regimens in contrast to a mixture of two mAbs (Chames and Baty, 2009; Hollander, 2009; Thakur and Lum, 2010). Recently, catumaxomab, a trifunctional bispecific antibody targeting human epithelial cell adhesion molecule (EpCAM) and CD3 has shown a clear clinical benefit in patients with peritoneal carcinomatosis of epithelial cancers (Heiss et al., 2010), and a bispecific T-cell engaging (BiTE) antibody with dual specificity for CD19 and CD3 has also demonstrated encouraging clinical activity in patients with CD19 expressing hematological malignancies (Bargou et al., 2008). Despite strong interest in the development of bispecific molecules as cancer therapeutics, technical challenges in the production of stable and active bispecific molecules have in the past hindered the clinical evaluation of most bispecific formats. Many engineered antibody formats, including an IgG-like bispecific antibody have compromised stability or solubility (Bargou et al., 2008; Demarest and Glaser, 2008; Lu et al., 2005). Furthermore, several strategies have been taken to increase the product quality and in vivo stability of bispecific molecules, including PEGylation, conjugation with human serum albumin and Fc engineering (Muller et al., 2007; Ridgway et al., 1996). Bispecific antibodies of the general form described above have the advantage that the nucleotide sequence encoding the two V-domains, single linker or one spacer can be incorporated into a suitable host expression organism under the control of a single promoter. This increases the flexibility with which these constructs can be designed as well as the degree of experimenter control during their production. In addition, the Fc of IgG is a very another attractive scaffold for designing novel therapeutics because it contains all antibody functions except the binding ability. Fc engineering is important for improving the effectiveness of the bispecific antibodies. Therefore, the IgG-based conformation is using in present invention for two independent target on immune cells or pro-angiogenic proteins in cancer therapy.

Targeting immune-check point proteins are promising approaches to activate antitumor immunity. Anti-check point proteins, such as PD-1, PD-L1, CTLA-4, LAG3, etc., are currently evaluated clinically (FIG. 1). Preliminary data with blockers of immune checkpoint proteins have been shown to be able to enhance antitumor immunity with the potential to produce durable clinical responses. However, despite the remarkable clinical efficacy of these agents in a number of malignancies, it has become clear that they are not sufficiently active for many patients. Numerous additional immunomodulatory pathways as well as inhibitory factors expressed or secreted by myeloid and stromal cells in the tumor microenvironment are potential targets for synergizing with immune checkpoint blockade. Therefore, combining anticancer or bispecific antibody therapies has been essential to achieve complete remission and cures for patients with cancer. Meanwhile, targeting VEGF already know to be reduced the angiogenesis by tumor (Hicklin and Ellis, 2005) and may help restore part of the cancer immunity cycle by increasing T-cell infiltration into the tumor microenvironment (Hughes et al., 2016; Terme et al., 2012; Wallin et al., 2016).

The extracellular ligand binding domain (SEQ ID NO: 1 and 2) of a human VEGF receptor is capable of binding to a VEGF ligand, and comprises one or more of Ig-like domains D1-D7 (Table 1) of one or more VEGF receptors. Preferably, the extracellular ligand binding domain of the VEGF receptor comprises an Ig-like domain D2 of a first VEGF receptor and an Ig-like domain D3 of a second VEGF receptor, wherein the first and second VEGF receptors are the same or different VEGF receptors. In present invention, VEGF inhibition domain (VID), the extracellular ligand binding domain of the VEGF receptor comprises an Ig-like domain D2 of a VEGFR1 and an Ig-like domain D3 of a VEGFR2 to block the VEGF and reduce the angiogenesis.

TABLE 1

The amino acid sequence of Ig-like domains of human VEGF receptors

| Name | SEQ ID NO. | Sequence |
| --- | --- | --- |
| D1 of human VEGF receptor 1 | 14 | PELSLKGTQHIMQAGQTLHLQCRGEAAHK WSLPEMVSKESERLSITKSA |
| D2 of human VEGF receptor 1 | 15 | GRELVIPCRVTSPNITVTLKKFPLDTLIPDG KRIIWDSRKGFIISNATYKEIGLLTCEATVN GH |
| D3 of human VEGF receptor 1 | 16 | IDVQISTPRPVKLLRGHTLVLNCTATTPLNT RVQMTWSYPDEKNKRASVRRRIDQSNSH ANIFYSVLTIDKMQNKDKGLYTCRVRSGPS FKSVNTSVH |
| D4 of human VEGF receptor 1 | 17 | TVKHRKQQVLETVAGKRSYRLSMKVKAFP SPEVVWLKDGLPATEKSARYLTRGYSLIIK DVTEEDAGNYTILLSIKQSNVFKNLTAT |
| D5 of human VEGF receptor 1 | 18 | PQIYEKAVSSFPDDPALYPLGSRQILTCTAY GIPQPTIKWFWHPCNHNHSEARCDFCSN NEESFILDADSNMGNRIESITQRMAIIEGKN KMASTLVVADSRISGIYICIASNKVGTVGRN ISFYIT |
| D6 of human VEGF receptor 1 | 19 | PNGFHVNLEKMPTEGEDLKLSCTVNKFLY RDVTWILLRTVNNRTMHYSISKQKMAITKE HSITLNLTIMNVSLQDSGTYACRARNVYTG EEILQ |
| D7 of human VEGF receptor 1 | 20 | PYLLRNLSDHTVAISSSTTLDCHANGVPEP QITWFKNNHKIQQEPGIILGPGSSTLFIERV TEEDEGVYHCKATNQKGSVESSAYLT |
| D1 of human VEGF receptor 2 | 21 | NTTLQITCRGQRDLDWLWPNNQSGSEQR VEVTECSDGLFCKTLTIPKVIGNDTGAYKC FYRETDL |
| D2 of human VEGF receptor 2 | 22 | NKNKTVVIPCLGSISNLNVSLCARYPEKRF VPDGNRISWDSKKGFTIPSYMISYAGMVF CEAKINDE |
| D3 of human VEGF receptor 2 | 23 | YDVVLSPSHGIELSVGEKLVLNCTARTELN VGIDFNWEYPSSKHQHKKLVNRDLKTQSG SEMKKFLSTLTIDGVTRSDQGLYTCAASS GLMTKKNST |
| D4 of human VEGF receptor 2 | 24 | FVAFGSGMESLVEATVGERVRIPAKYLGY PPPEIKWYKNGIPLESNHTIKAGHVLTIMEV SERDTGNYTVILTNPISKEKQSHVVS |

TABLE 1-continued

The amino acid sequence of Ig-like domains of human VEGF receptors

| Name | SEQ ID NO. | Sequence |
| --- | --- | --- |
| D5 of human VEGF receptor 2 | 25 | PQIGEKSLISPVDSYQYGTTQTLTCTVYAIP PPHHIHWYWQLEEECANEPSQAVSVTNP YPCEEWRSVEDFQGGNKIEVNKNQFALIE GKNKTVSTLVIQAANVSALYKCEAVNKVG RGERVISFHVT |
| D6 of human VEGF receptor 2 | 26 | PEITLQPDMQPTEQESVSLWCTADRSTFE NLTWYKLGPQPLPIHVGELPTPVCKNLDTL WKLNATMFSNSTNDILIMELKNASLQDQG DYVCLAQDRKTKKRHCVVRQLT |
| D7 of human VEGF receptor 2 | 27 | PTITGNLENQTTSIGESIEVSCTASGNPPP QIMWFKDNETLVEDSGIVLKDGNRNLTIRR VRKEDEGLYTCQACSVLGCAKVEAFFI |

In some embodiments, the VEGF inhibiting domain comprising an amino acid sequence of at least about 80% sequence homology to the amino acid sequence selected from the group consisting of SEQ ID NO: 1, 2, 9, 14, 15, 16, 17, 18, 19, 20, 21, 22, 23, 24, 25, 26, 27, and a combination thereof. In some examples, the VEGF inhibiting domain comprises an amino acid sequence of at least about 85%, 90%, or 95% sequence homology to the amino acid sequence as above mentioned.

The present invention describes the construction, expression and characterization of anti-immune checkpoint protein antibody Fc fused with VEGF inhibition domain (VID) from human VEGF receptor. The N-terminally positioned anti-PD-L1 antibody in fusion constructs shall allow expanding the power of fusion proteins beyond immune potentiating agent if the fusion counterpart is replaced by other immune checkpoints, such as anti-CTLA-4, CD3, OX40 antibodies or cell surface targeting molecule such as anti-EGFR, anti-HER2, and anti-CD40 antibodies for example.

The present disclosure provides bispecific antibody or antigen-binding portion thereof, comprising a binding domain binding cell surface protein; and a vascular endothelial growth factor (VEGF) inhibiting domain. In some embodiments, the binding domain binding the PD-L1 comprises: a heavy chain variable domain and a light chain variable domain. The heavy chain variable domain comprising an amino acid sequence of at least about 80% sequence homology to the amino acid sequence selected from the group consisting of SEQ ID NO: 4 and 6. In some examples, the heavy chain variable region comprises an amino acid sequence of at least about 85%, 90%, or 95% sequence homology to the amino acid sequence as above mentioned. The light chain variable domain comprising an amino acid sequence of at least about 80% sequence homology to the amino acid sequence selected from the group consisting of amino acid 1-111 of SEQ ID NO: 3 and 1-110 of SEQ ID NO: 5. In some examples, the light chain variable region comprises an amino acid sequence of at least about 85%, 90%, or 95% sequence homology to the amino acid sequence as above mentioned.

Antibody Generation from OmniMab Library

Figure 2A:
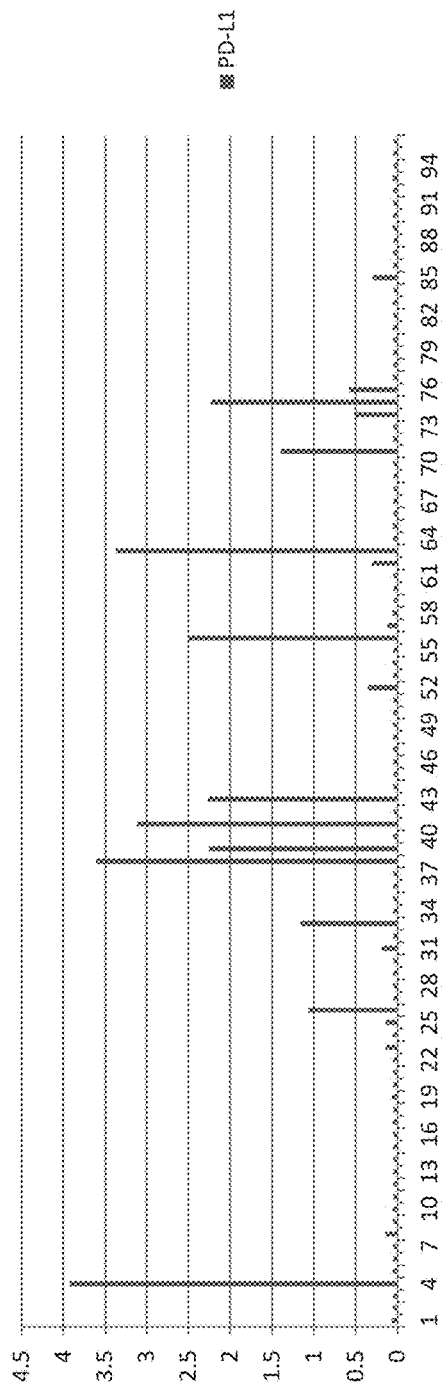
FIGS. 2A and 2B show the screening of phage clones by direct ELISA for recombinant PD-L1.
Figure 2B:
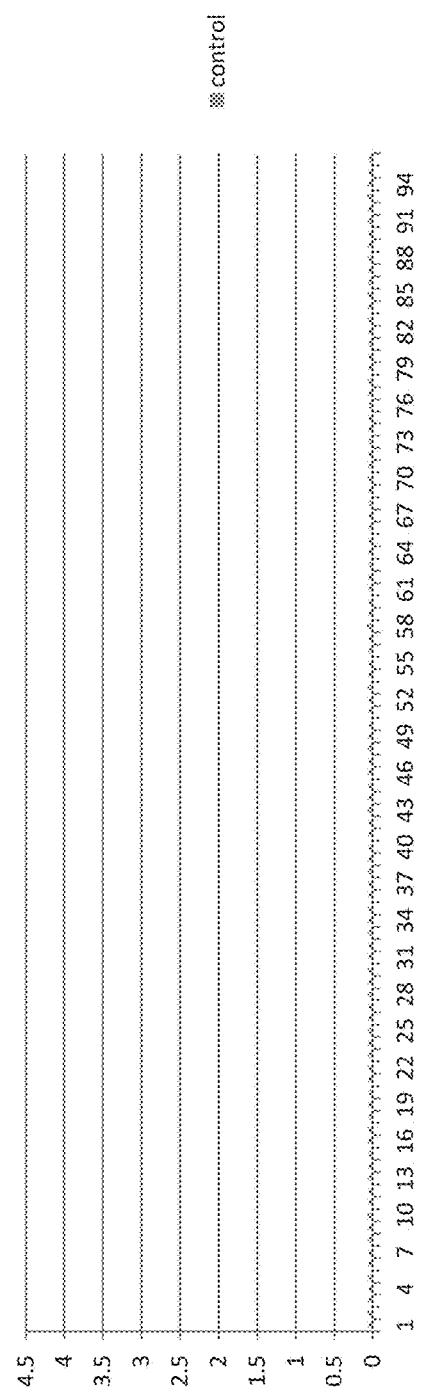

For the generation of therapeutic antibodies against PD-L1, selections with the OmniMab phagemid library were carried out. The phagemid library is generated by AP Biosciences Inc. (APBio Inc.) from a collection of over hundred health donors B cells. Phages for the 1st round of pannings were prepared by Hyperphage (M13K07ΔpIII, Progen, Heidelberg, Germany). Solid phase panning and cell panning against PD-L1 were applied for PD-L1 specific binder selection and isolation from OmniMab library. Solid phase panning was performed using recombinant human PD-L1-Fc (APBio Inc.) in the first round selection and then HEK293 cells expressed PD-L1 were used for additional two rounds enrichment. After three rounds selection, the specific PD-L1 binders were screened and isolated by direct ELISA with corresponding recombinant protein (FIGS. 2A and 2B). Pre-coated PD-L1-Fc recombinant proteins were blotted with supernatant containing rescued phages for 1 hour and washed with PBS containing 0.1% Tween-20 for three times. Bound phages were detected by HRP conjugated anti-M13 antibody (Roche) and TMB substrate was used for signal development. The $OD_{450}$ readings were recorded. The positive binders were isolated and sent for sequencing to confirm the sequence and diversity of heavy chain and light chain. The variable region of heavy chain and light chain specific to PD-L1 were described from the SEQ ID NO: 3 to SEQ ID NO: 6: SEQ ID NO: 3 is the light chain of PD-L1 clone 6, SEQ ID NO: 4 is the variable region of heavy chain of PD-L1 clone 6, SEQ ID NO: 5 is the light chain of PD-L1 clone 32, SEQ ID NO: 6 is the variable region of heavy chain of PD-L1 clone 32. As shown in the FIGS. 2A and 2B, several clones were isolated and known to be recognized specifically for corresponding antigen as comparing with negative control.

Figure 3:
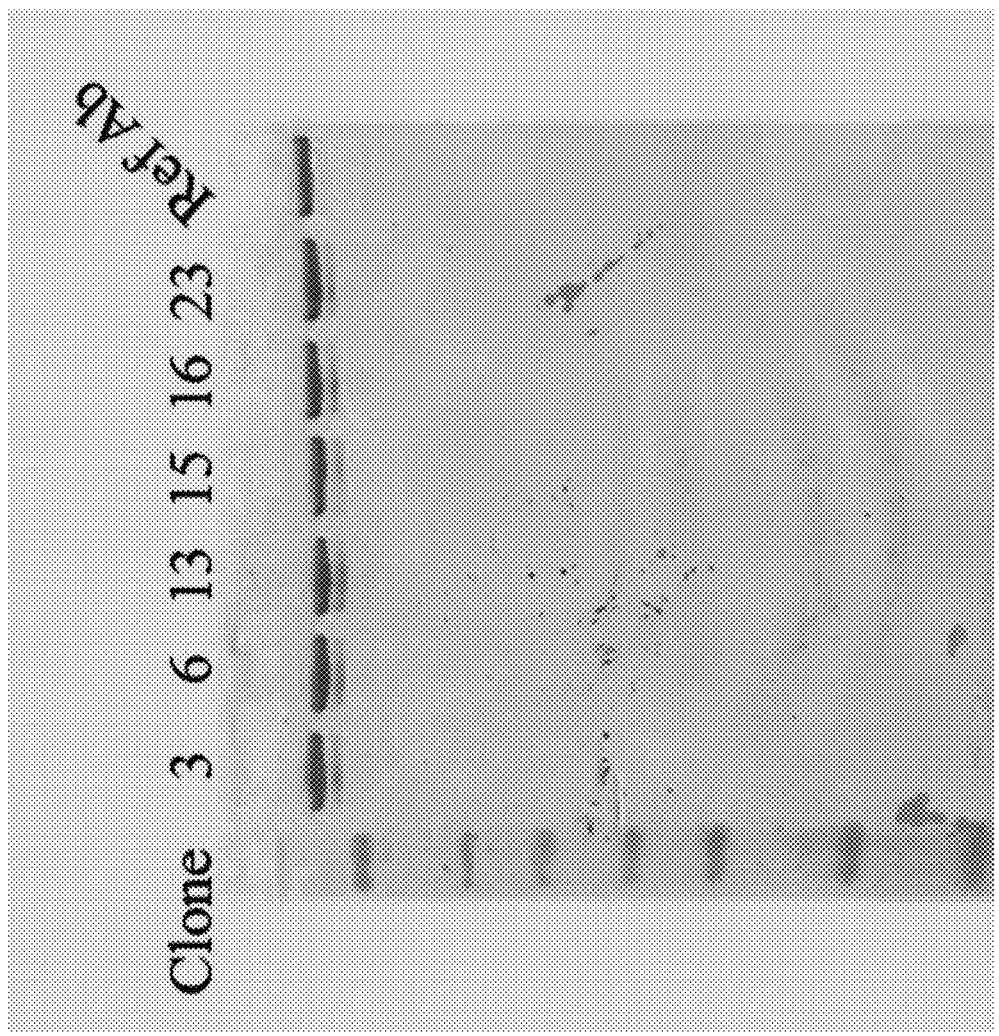
FIG. 3 shows purified antibody leads specific for PD-L1 by SDS-PAGE with non-reducing to reveal the integrity and purity.

Subcloning and Expression/Purification of Selected PD-L1 Specific Binder as IgG Format To facilitate the quick screening of specific binder with functionality in T cell activation, the heavy chains and light chains of positive binders against PD-L1 by ELISA were then amplified, digested and sub-clone into APBio specialized IgG expression vector carrying IgG4 constant region (SEQ ID NO: 7). After sequence validation, the plasmids were then prepared and transfected into HEK293 cells for antibody expression with 293 fectin transfection reagent (Invitrogen). After 4 days culture, the antibody secreted into serum-free medium is affinity purified from culture supernatant by Protein G chromatography. Purified antibody is then concentrated, followed by dialysis in PBS buffer. The final concentration of dialyzed protein is determined by NanoDrop2000 spectrophotometer and the purity and integrity are determined by SDS-PAGE without reducing reagent as shown in the FIG. 3. The integrity of various purified antibody leads is normal in the HEK293 cells as well as reference antibody, MPDL3280A.

Binding Activity Determination for PD-L1 Specific IgG Leads by Direct ELISA

Figure 4:
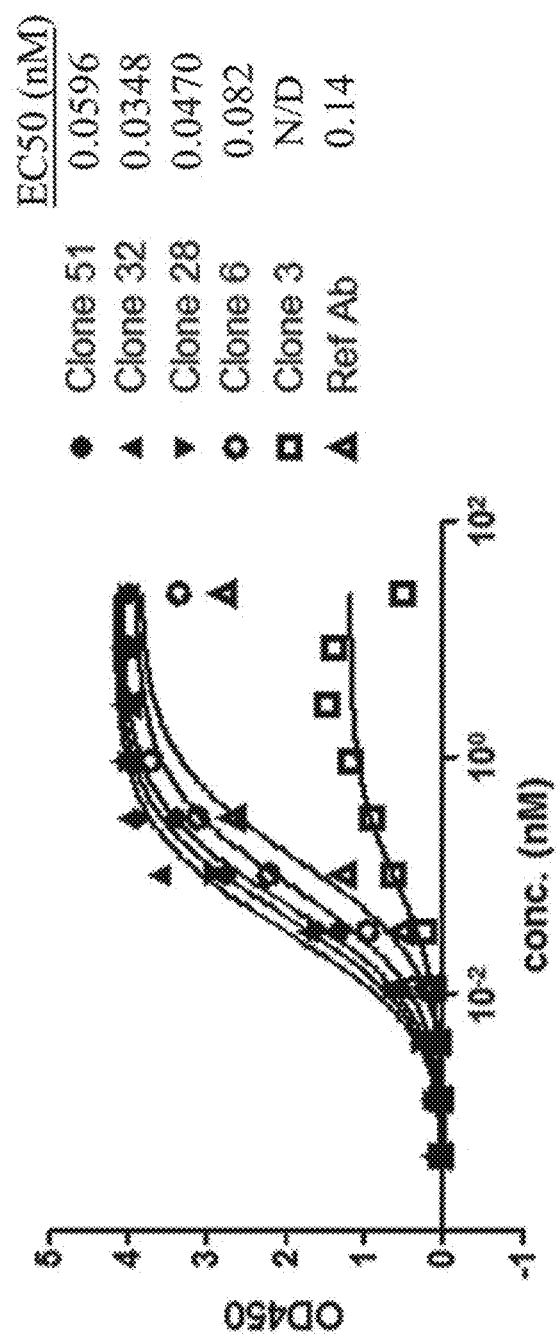
FIG. 4 shows examples of the direct ligand binding activity of purified anti-immune check point proteins and anti-PD-L1 antibody leads against PD-L1. Ligand pre-coated wells were first incubated with various concentrations of antibody leads as indicated. The bound proteins were then detected with HRP conjugated goat anti-human IgG Fab specific antibody and $OD_{450}$ readings were plotted.

Purified antibody leads against PD-L1 (anti-PD-L1 antibody leads) were then applied for ELISA binding characterization on human PD-L1-Fc in a direct coated setup. FIG. 4 showed the ELISA binding result for anti-PD-L1 antibodies. For PD-L1 specific antibodies, most leads showed a similar or better binding activity with reference antibody (Ref Ab, MPDL3280A, Roche).

Purified human PD-L1 IgG1 Fc chimera (PD-L1-Fc, APBio) was dialyzed in Phosphate Buffered Saline (PBS), adjusted to 1 mg/mL and then diluted with PBS to a final concentration of 1 μg/mL. Nunc-Immuno Maxisorp 96 well plates were coated with 0.1 mL per well of recombinant PD-L1-Fc chimera leaving empty wells for nonspecific binding controls and incubated at 4° C. overnight. The PD-L1-Fc chimera solution was removed and the plates were washed three times with 0.4 mL wash buffer (0.1% Tween-20 in PBS). 0.4 mL blocking buffer (5% low-fat milk powder in PBS) was added to all wells and incubated at room temperature for 1 hour with mixing. The blocking buffer was removed and plates washed three times with 0.4 mL wash buffer. Serial dilutions of the PD-L1 test antibodies were prepared in PBS and 0.1 mL diluted Ab was added per well. Plates were incubated 1 hour at room temperature. Antibody solution was removed and the plates washed three time with 0.4 mL wash buffer per well. Horseradish peroxidase labeled goat anti-human IgG, F(ab')$_2$ specific F(ab')$_2$ antibody (Jackson Immunoresearch #109-036-097) was diluted 1:2000 with PBS and added 0.1 mL per well. The plates were incubated 1 hour at room temperature and washed with 0.4 mL per well wash buffer. 0.1 mL TMB reagent (Invitrogen) was added and incubated for 1 to 5 minutes at room temperature. The reaction was stopped by adding 0.05 mL 1N HCl and absorbance was read at 450 nm on a Bio-Tek Spectra. Calculated EC50 for anti-PD-L1 antibody leads to PD-L1 showed most leads possess good binding activity as well as MPDL3280A (Ref Ab) by direct ELISA (FIG. 4).

Binding Activity Determination for PD-L1 Specific IgG Leads by FACS

Figure 5:
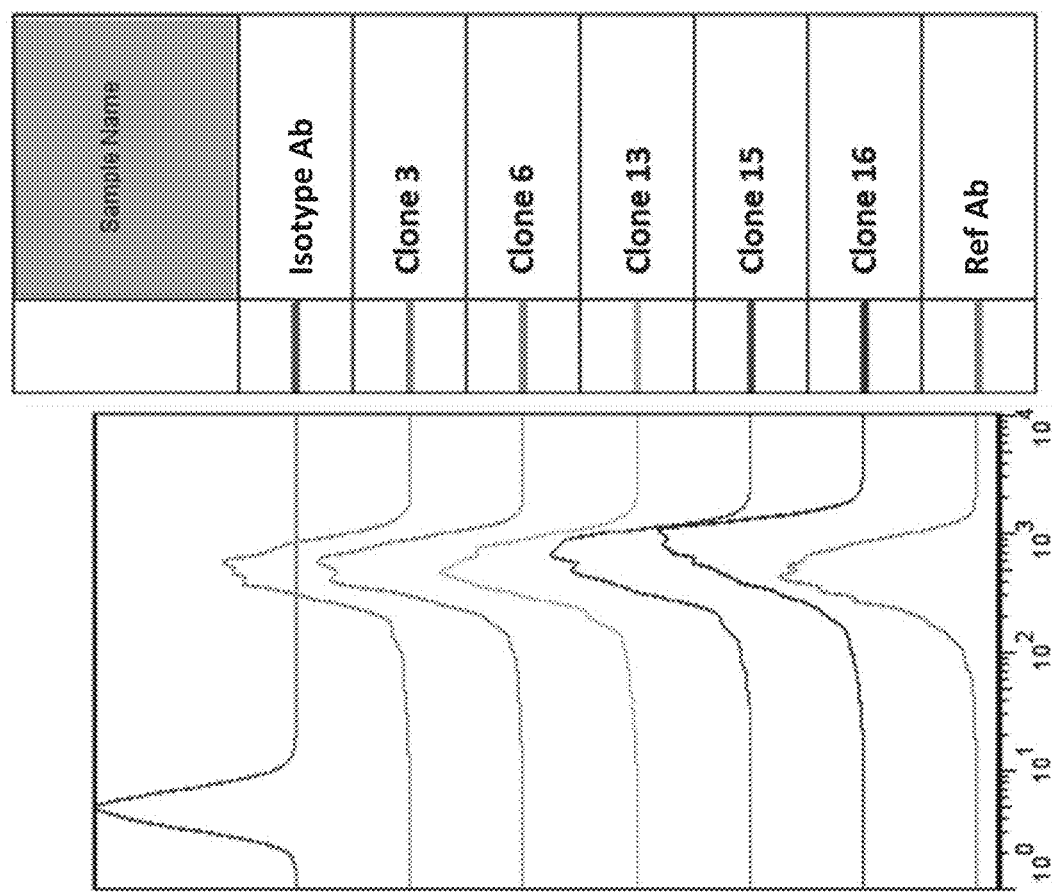
FIG. 5 shows the flow analysis using PD-L1 expression 293 cells. PD-L1 expression HEK293 cells were first incubated with purified antibody leads, and the bound antibodies were detected with Alexa-488 conjugated goat anti-human IgG (H+L) followed by fluorescence-activated cell sorter (FACS) analysis.

Purified antibody leads (anti-PD-L1 antibody leads) were also applied for flow cytometry to determine and compare the binding activity with PD-L1 expressed HEK293 cells. FIG. 5 show the binding activity of corresponding antibody leads as indicated by FACS with stable expressed PD-L1 HEK293 cells.

FACS analysis of PD-L1 stable expression 293 cells stained with anti-PD-L1 antibody leads to examine the PD-L1 binding activity, stable expression cells were incubated with 1 µg/mL purified anti-PD-L1 antibody leads, reference antibody (Ref Ab MPDL3280A) or with isotype antibody as negative control on ice for 1 hr. The cells were washed three times with 1×PBS and then incubated with Alexa-488-conjugated goat anti-human IgG (H+L) (Invitrogen Inc.) on ice for additional 1 hr. After staining, the cells were washed three times with 1×PBS, resuspended in 1×PBS/2% FBS before analyzed by FACS Calibur (BD Biosciences, Inc.) and FlowJo (TreeStar, LLC). As shown in the FIG. 5, most anti-PD-L1 antibody leads possess a good binding activity as well as reference antibody. This indicated the phage clones selected from the OmniMab library indeed recognize the native PD-L1 in the cells.

Ligand Competition Binding (ELISA Assay)

Antibody leads were showed the binding selectivity and affinity assay used to evaluate the anti-PD-L1 antibody leads of present invention for their ability to block binding of PD-L1 to PD-1.

Figure 6:
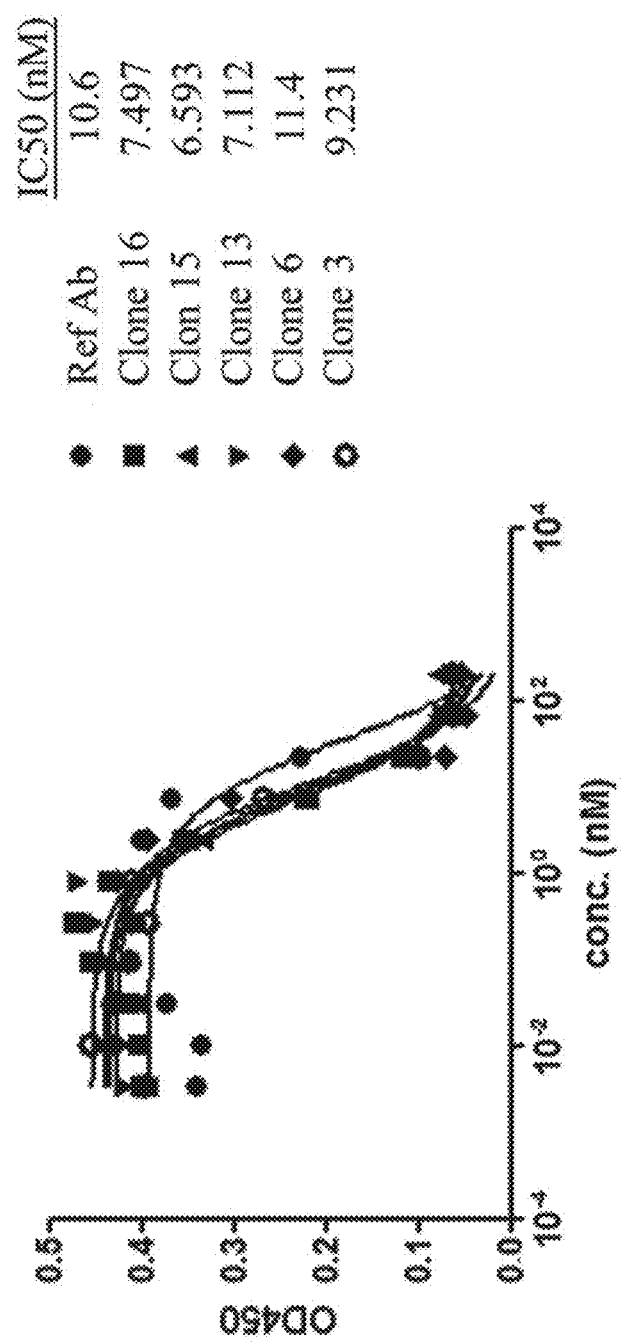
FIG. 6 shows the blockage of PD-1/PD-L1 interaction with purified anti-PD-L1 antibodies. Purified antibodies as indicated were applied with biotinylated-PD-L1-Fc and pre-coated PD-1/His in 96-well plate to evaluate the inhibition activity of PD-1/PD-L1 interaction. The binding recombinant PD-L1-Fc on recombinant PD-1 was detected by streptavidin-HRP and analysis by ELISA.

Antibodies were tested for their ability to block the binding of the human PD-L1-Fc chimera (PD-L1-Fc) to recombinant human PD-1/His (hPD-1/His) by ELISA. Purified recombinant hPD-1/His (APBio) was dialyzed to 1 mg/mL in PBS and then conjugated with biotin (Abcam). Nunc Maxisorp 96 well plate was coated with 250 ng hPD-1/His per well in PBS overnight. The hPD-1/His solution was removed and the plates were washed three times with 0.4 mL wash buffer (0.1% Tween-20 in PBS). 0.4 mL blocking buffer (5% low-fat milk powder in PBS) was added to all wells and incubated at room temperature for 1 hour with mixing. During the blocking step the antibody stocks were diluted in a range from 200 nM to 0 nM in PBS with 2 folds serial dilution. Purified recombinant biotinylated-PD-L1-Fc chimera was diluted to 4 µg/mL in PBS. The PD-1/His coated plates were washed three times with 0.2 mL wash buffer (0.1% Tween 20 in PBS). 60 µL antibody dilutions (anti-PD-L1 antibody leads or Ref Ab MPDL3280A) were added alone with 60 µL biotinylated-PD-L1-Fc chimera and incubated at room temperature for 1 hour. Plates were washed as described previously. Strepta-vidin-HRP was diluted 1:2000 in PBS, 100 µL of the resulting solution added to the wells of the washed plated, and incubated at room temperature for 1 hour. Plates were washed as previously described, 100 µL TMB substrate solution was added to each well and incubated for 10 minutes. The reaction was stopped with 50 µL 1N HCl and absorbance at 450 nm read using Bio-Tek reader and showed in FIG. 6. Partial antibody leads are showed to inhibit the interaction between PD-1-PD-L1 by competition ELISA. Most antibody leads revealed a similar blocking activity as comparing with reference antibody (Ref Ab MPDL3280A).

Enhanced Stimulation of T Cell Activation by Inhibition of PD-1:PD-L1 Ligand Interaction for Anti-PD-L1 Antibody The PD-1 signaling pathway inhibits moderate TCR/CD28 costimulatory signals, with cytokine production being reduced first without a decrease in T cell proliferation. As the TCR/CD28 costimulatory signals weaken, the PD-1 pathway dominates, with a great reduction in cytokine production accompanied by a reduction in proliferation. Accordingly, in order to confirm that the inhibition of the PD-1 via inhibition of the interaction with PD-L1, human antibodies of the invention enhances T cell activation, mixed lymphocyte reactions (MLRs) are performed.

Monocytes from human whole blood were enriched by RosetteSep™ Human Monocyte Enrichment Cocktail (Cat. No. 15068) and cultured in differentiation medium, RPMI 1640 with 10% FBS, 100 ng/mL (1000 U/mL) GM-CSF, 100 ng/mL (500 U/mL) for 6 days. The differentiate dendritic cells (DC) from monocyte were checked by DC-SIGN-PE, anti-CD14 conjugated with FITC Ab, anti-CD83 conjugated with PE Ab, or anti-CD80 conjugated with FITC Ab to validate the differentiation and used to be APCs in MLRs.

Figure 7:
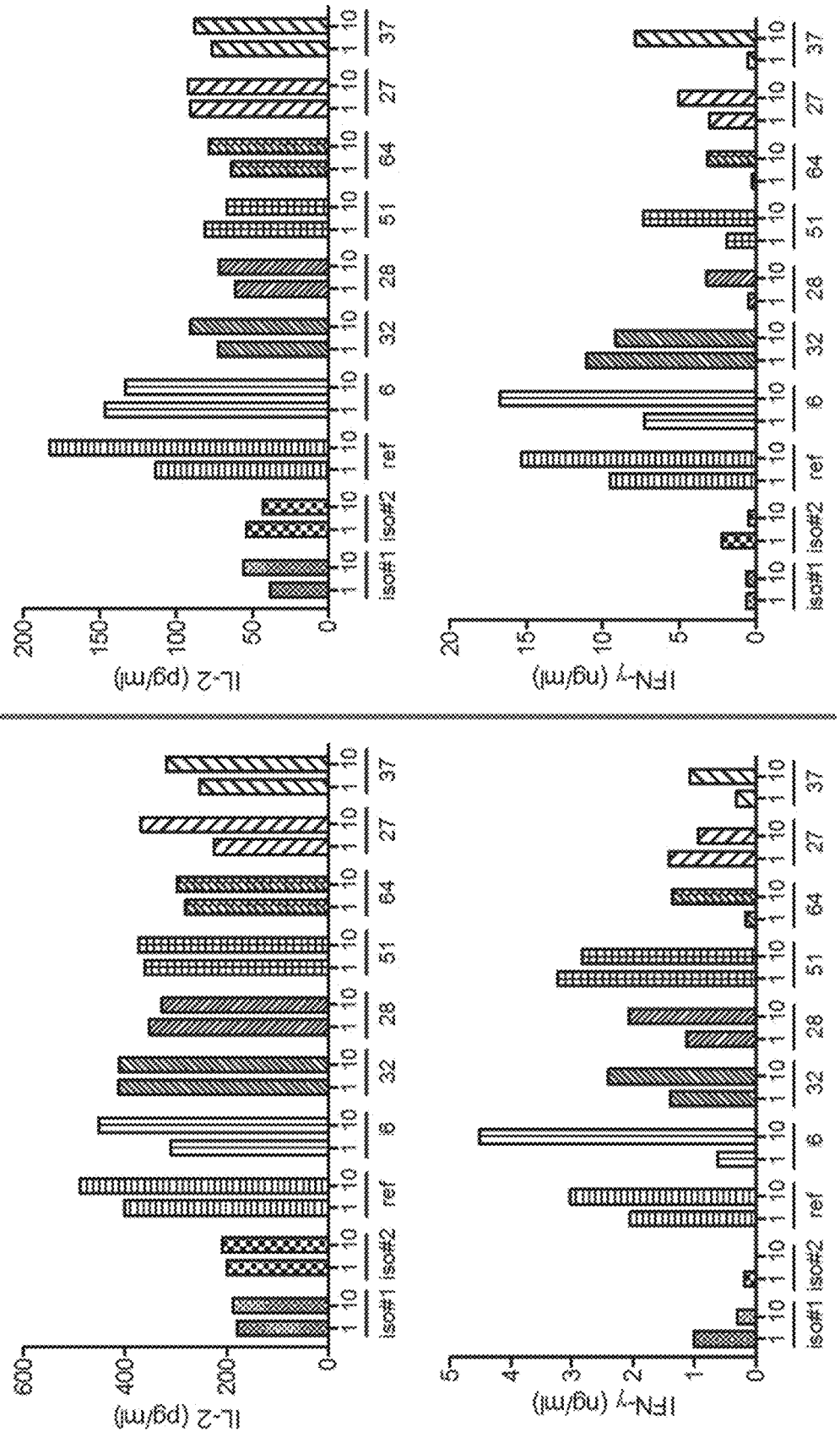
FIGS. 7A and 7B show anti-PD-L1 antibody leads with 1 or 10 μg/mL stimulates IL-2 and/or IFN-γ production in a mixed lymphocyte reaction (MLR) assay after 3 days (FIG. 7A) or 5 days (FIG. 7B) antibody treatment.

Allogenic CD4$^+$ T cells from human whole blood were isolated by RosetteSep™ Human CD4$^+$ T Cell Enrichment Cocktail (Cat. NO. 15062). The purity of CD4$^+$ T cells were checked with anti-CD4 conjugated APC Ab to make sure the purity is above 95% and then labeled with 1 µM CFSE (CellTrace™ CFSE cell proliferation kit, Life technologies, Cat. NO. C34554) for T cells proliferation assay. Labeled CD4$^+$ T cells were used to co-culture with immature DC with different antibody leads as indicated for 3 and 5 days to see whether the antibody leads could restore the T cell activation through blocking the interaction between PD-1 and PD-L1. After 3 and 5 days incubation, the supernatant were collected for cytokine, such as IL-2 and IFN-γ quantitation by ELISA. The addition of anti-PD-L1 antibody leads (clones 6, 32, 28, 51, 64, 27, and 37) to cultures of immature dendritic cells plus allogeneic T cells is predicted to result in an increase in T cell proliferation and cytokine production, as compared to isotype IgG (iso #1, #2) treated cultures and showed in the FIGS. 7A and 7B. The IL-2 and IFN-γ production increase significantly in the MLRs as comparing with isotype antibody treatment after 3 days (FIG. 7A) or 5 days (FIG. 7B) antibody treatment, especially for anti-PD-L1 antibody clone 6. The cytokine increment is still obviously after 5 days antibody treatment and similar to reference antibody (ref), MPDL3280A. This indicated the anti-PD-L1 antibody clone 6 should be one of the potential leads for bispecific antibody composite.

Construction, Expression and Purification of Anti-PD-L1-VID Antibody

Since the bispecific is designed as IgG based fused with VEGF inhibition domain, the anti-PD-L1 antibody clone 6 is assigned to be IgG form, on the other hand, the VEGF binding domain, D1 and D2, in VEGF receptor is fused at C-terminal of Fc region in anti-PD-L1 clone 6 antibody. Since Fc isotype or engineered Fc is important for improving the effectiveness or production of the bispecific antibodies in mammalian cells; therefore, two different Fc isotype, IgG4 (SEQ ID NO: 7) and engineered IgG1 (eIgG1, reduction of antibody-dependent cell-mediated cytotoxity (ADCC), SEQ ID NO: 8) were used to bispecific construction. Construction of bispecific anti-PD-L1 antibody Fc fused with VID (SEQ ID NO: 9) was depicted in FIG. 8. A short flexible peptide linker, (GGGGS)$_3$ (SEQ ID NO: 10) was placed between, for example, anti-PD-L1 antibody heavy chain C-terminal of Fc region (SEQ ID NO: 4) and N-terminal module of VID to ensure correct folding and minimize steric hindrance. The coding sequences of anti-PD-L1-VID heavy chain for IgG4 and eIGg1 were shown in SEQ ID NO: 12 and NO: 13. The constructed antibody Fc fusion proteins were leaded by a signal peptide (SEQ ID NO: 11) and expressed by mammalian cells, and purified from the transfected cell culture supernatant via 1-step Protein G chromatography. As shown in FIG. 9, greater than 95% purity can be obtained in a single step purification process and shows that purified fusion proteins have correct molecular weight (Mw=220 kDa). Since the low purity or recovery rate is the main issue for the bispecific antibody or fusion protein production in the chemistry, manufacturing, and controls (CMC) production; therefore, both purified bispecific antibodies were also applied for size elusion column (SEC) with high-performance liquid chromatography (HPLC) to evaluate the purity of bispecific antibodies (FIGS. 10A and 10B). Both bispecific antibodies, either anti-PD-L1-VID/IgG4 (FIG. 10A) or anti-PD-L1-VID/eIgG1 (FIG. 10B), revealed the purity is higher than 99% purity in the SEC-HPLC analysis. It implicated the format could be processed easily in the CMC development and provide the successful rate in the further development.

Figure 8:
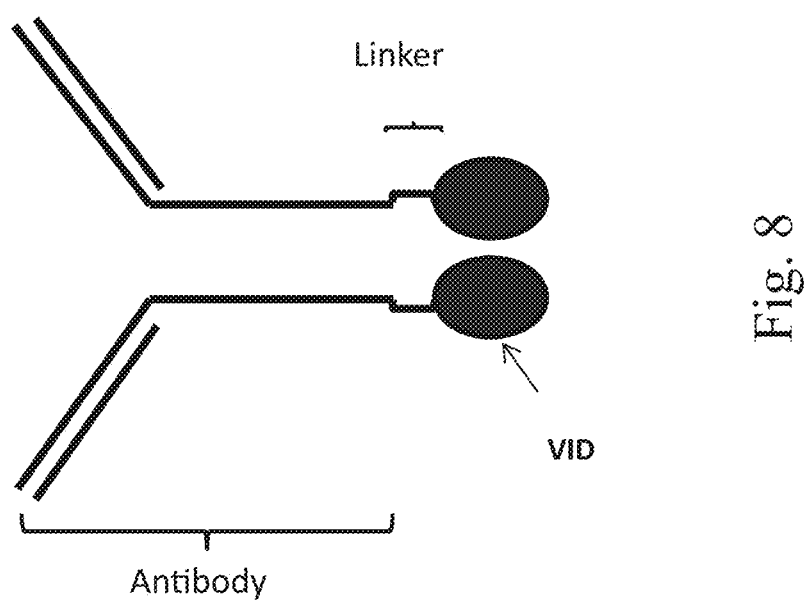
FIG. 8 shows the structure of an antibody heavy chain Fc fused with VEGF inhibition domain (VID) from VEGF receptor.
Figure 9:
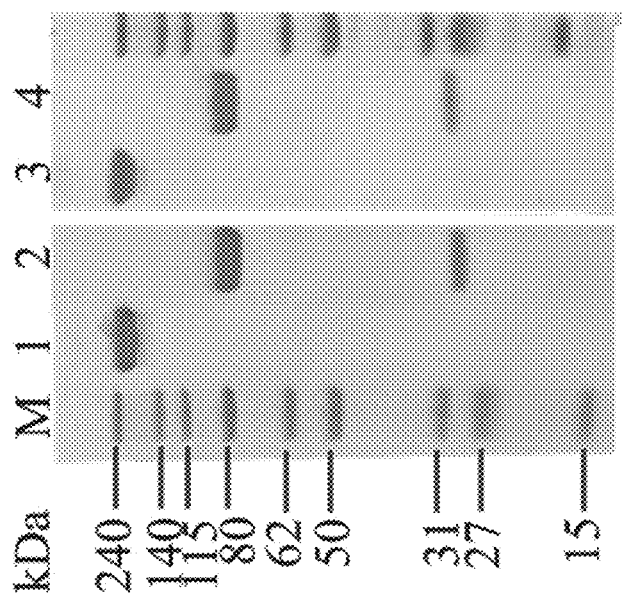
FIG. 9 shows examples of PAGE-gel analysis of anti-immune check point antibodies-VID bispecific antibodies. Purified fusion proteins, anti-PD-L1-VID bispecific antibodies were shown to have a molecular weight about 220 kDa (non-reducing), and heavy chain fusion has about 85 kDa and light chain is about 25 kDa (reduced) in both antibody fusions. M is marker, Lane 1 is non-reduced anti-PD-L1-VID/eIgG1, Lane 2 is reduced anti-PD-L1-VID/eIgG1, Lane 3 is non-reduced anti-PD-L1-VID/IgG4, and Lane 2 is reduced anti-PD-L1-VID/IgG4. Each of lanes loads 3 μg.

As shown in FIG. 8, the structure of anti-immune checkpoint antibody Fc-terminally fused with VID. In some embodiments, antibody can be inhibitory anti-immune checkpoint antibodies, such as anti-PD-L1, anti-PD-1, anti-CTLA4, anti-LAG3, etc., or stimulatory antibodies, such as anti-CD28, anti-CD137, anti-CD27, anti-ICOS, etc. or cell surface receptor/antigen, such as HER2, EGFR etc. A linker is placed between antibody Fc and VID to generate the bispecific antibody.

Binding Affinity of the Fusion Proteins to PD-L1 and VEGF$_{165}$

A direct binding enzyme-linked immunosorbent assay (ELISA) was used to measure the binding affinity of the bispecific antibodies to PD-L1 or VEGF$_{165}$, a splice variant of VEGF-A. A recombinant VEGF trapping protein (VEGFR-Fc) and parental anti-PD-L1 antibody clone 6 was used as positive control 1 for PD-L1 and VEGF, respectively. VEGFR-Fc, aflibercept, is a soluble VEGF receptor that was engineered for therapeutic use and is currently approved by U.S. food and drug administration (FDA) to treat age-related macular degeneration (AMD). VEGFR-Fc contains the second Ig-like domain (D2) of VEGFR1 fused to the third Ig-like domain (D3) of VEGFR2 fused to the Fc region of human IgG1 (Holash et al., 2002).

100 μL of a coating solution (1 μg/mL VEGF$_{165}$ in phosphate buffered saline (PBS), pH 7.2) were added to each well of a 96-well ELISA plate, and the plate was incubated overnight at 4° C. The wells were washed twice with 400 μL PBS buffer, and excess liquid was carefully removed with a paper towel. 400 μL of a blocking solution (5% non-fat skim milk in PBS) was added to each well, and the plate was incubated at room temperature for 1 hour. The wells were washed twice with PBS buffer. Bispecific antibody and control samples were serially diluted three-fold in blocking solution, with the highest protein concentration of 100 nM. 100 μL of the serially diluted samples were added to each well. The plate was covered and incubated on a plate shaker (about 100 rpm) for 1 hour at room temperature. The wells were washed three times with wash buffer (0.05% Tween-20 in PBS). 100 μL of 1:2500 diluted horseradish peroxidase-conjugated goat anti-human IgG Fc specific antibodies in blocking solution were added to each well. The plates were sealed and incubated on a plate shaker for 1 hour at room temperature. The plates were washed three times with wash buffer. 100 μL TMB substrate was added to each well, and the plates were incubated for 3 to 5 minutes to allow for the reaction to take place. To stop the reaction, 100 μL of stop solution (1N HCl) was added to each well. The optical density (OD) of each well was determined using an ELISA plate reader (Bio-Tek) at an absorbance wavelength of 450 nm. The absorbance was plotted against the protein concentration of the fusion protein or the control, and the concentration at which the signal was half the maximal effective concentration (EC50) was determined. Meanwhile, the binding activity of PD-L1 for both bispecific antibodies was also performed as a similar scenario as described above, except the bound bispecific antibodies were detected by horseradish peroxidase-conjugated goat anti-human IgG, F(ab')2 specific F(ab')2 antibody.

As the data shown in the FIG. 11A, the binding affinity, expressed as the EC50 value, was 0.075 for both anti-PD-L1-VID/IgG4 and anti-PD-L1-VID/eIgG1 antibodies for recombinant PD-L1 protein. Both bispecific antibodies possess a comparison binding activity as well as positive control, anti-PD-L1 clone 6 antibody (0.1 nM). Meanwhile, the result was also recorded for the VEGF binding activity test. As the data shown in the FIG. 11B, both bispecific antibodies showed a similar VEGF binding activity as compared with the positive control, VEGFR-Fc (aflibercept). The binding activity is not affected in both bispecific antibodies either for PD-L1 or for VEGF binding activity.

Inhibition of HUVEC Proliferation by the Anti-PD-L1-VID Bispecific Antibodies

Figure 12:
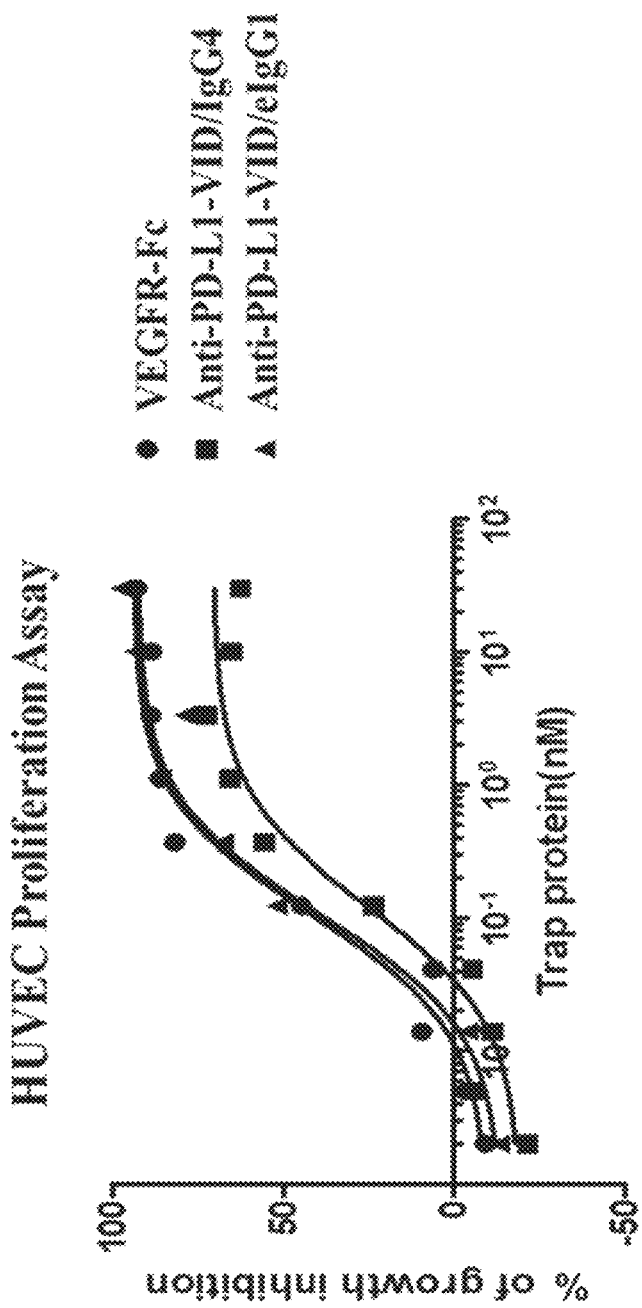
FIG. 12 shows the inhibition of $VEGF_{165}$-stimulated HUVEC proliferation with by purified anti-PD-L1-VID bispecific antibodies. $VEGF_{165}$ were pre-incubated with test samples as indicated for one day and then applied for HUVEC cells to monitor $VEGF_{165}$-stimulated HUVEC cell proliferation. After 3 days culture, the cell proliferation was determined by MTS reagent (Promega). The absorbance was plotted against the Abs concentration of the test sample, and the concentration at which the cell proliferation was inhibited by 50% ($IC_{50}$) was determined.

A human umbilical vein endothelial cell (HUVEC) proliferation assay was carried out to test the functionality of the bispecific antibody in the invention. VEGFR-Fc was used as a positive control as described above. 100 μL of a coating solution (1% gelatin in double distilled water) were added to each well of a 96-well ELISA plate, and the plate was incubated for 2 hours or overnight at 37° C. The wells were washed twice with PBS buffer. 3500 cells of HUVEC cells in endothelial cell growth medium were added to each well, and the plate was incubated overnight at 37° C. Sample as indicated were diluted in assay buffer (Medium-199 1× Earle's Salts, 10% fetal bovine serum, 10 mM HEPES, 1× antibiotic/antimycotic), with a highest protein concentration of 30 nM. The samples were mixed with VEGF$_{165}$ (8 ng/mL), and the mixtures were incubated overnight at room temperature. The wells were then washed with 200 μL PBS. 100 μL VEGF$_{165}$/sample mixture were added to each well, and the plates were incubated for 72 hours at 37° C. with 5% CO2. Following incubation, 10 μL MTS detection reagent (3-(4,5-dimethylthiazol-2-yl)-5-(3-carboxymethoxyphenyl)-2-(4-sulfophenyl)-2H-tetrazolium)+phenazine methosulfate in distilled PBS) was added to each well, and the plates were incubated at 37° C. for 2.5 hours. The OD of each well was determined using an ELISA plate reader (Bio-Tek) at an absorbance wavelength of 490 nm. The absorbance was plotted against the protein concentration of the test sample, and the concentration at which the cell proliferation was inhibited by 50% (1050) was determined. The inhibition of cell proliferation (1050) was determined to be between 0.1070 and 0.1233 nM for the tested fusion proteins of the invention. One of the bispecific antibodies, anti-PD-L1-VID/eIgG1, revealed a better inhibition than another bispecific antibody, anti-PD-L1-VID/IgG4 (FIG. 12, 0.1070 nM vs. 0.1233 nM). The 1050 of anti-PD-L1-VID/eIgG1 is good as well as positive control, VEGFR-Fc (0.1072 nM).

Figure 13B:
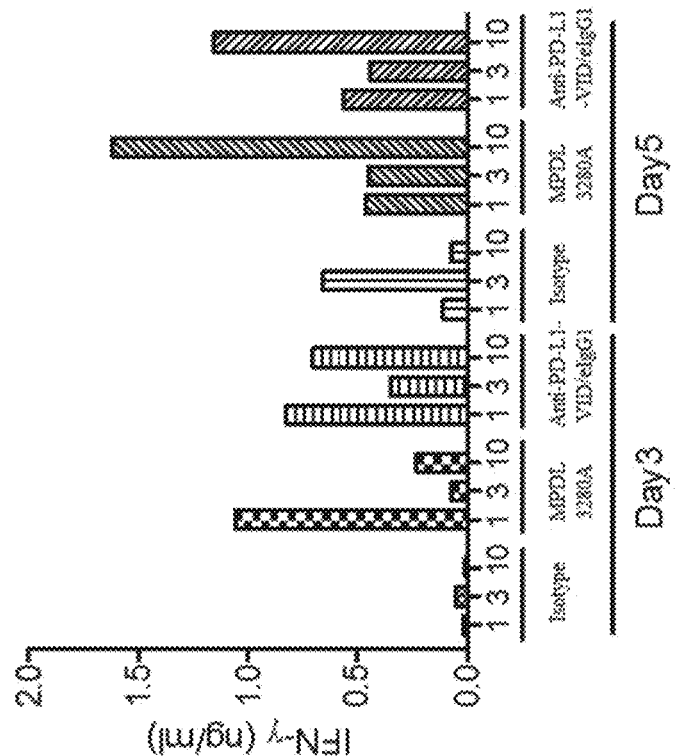
FIGS. 13A and 13B show bispecific antibody synergic stimulates T-cell activation for IL-2 (FIG. 13A) and IFN-γ (FIG. 13B) production in a mixed lymphocyte reaction (MLR) assay after 3 or 5 days with isotype IgG, reference antibody (MPDL3280A) or anti-PD-L1-VID/eIgG1 bispecific antibody treatment.
Figure 13A:
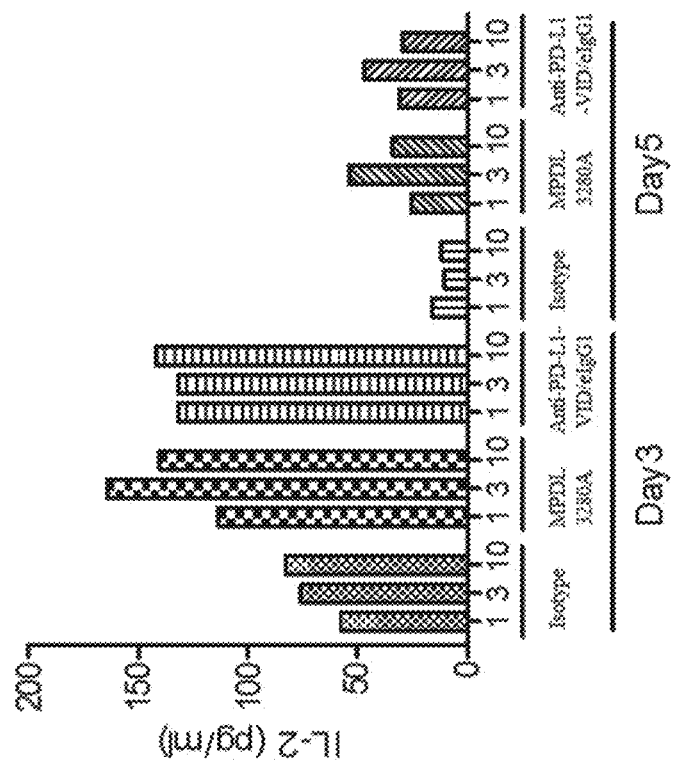

Enhanced Stimulation of T Cell Activation for Anti-PD-L1-VID/eIgG1 Bispecific Antibody Leads in MLRs To determine the antagonistic functionality of bispecific antibody in enhancing T cells activation through inhibition the interaction between PD-1 and PD-L1. The bispecific antibody leads, anti-PD-L1-VID/eIgG1 antibody, were applied into MLRs as described above. IL-2 and IFN-γ production were then recorded after 3 or 5 days antibody treatment. Mono- or bispecific antibody was applied as an equal mole to compare the antagonistic functionality in T cell activation enhancement and isotype IgG was used a negative control. As the data shown in the FIGS. 13A and 13B, the anti-PD-L1-VID/eIgG1 antibody showed a significant IL2 induction after 3 days treatment and dropped down after 5 days treatment. The profile of cytokine production is highly similar with the reference antibody, MPDL3280A. Meanwhile, the IFN-γ production is also upregulated and accumulated in the bispecific antibody leads treatment after 3 or 5 days treatment. This indicated the anti-PD-L1-VID/eIgG1 bispecific antibody also possess antagonistic functionality in T cell activation as well as reference antibody without loss any activities in the present invention.

In Vitro Serum Stability of Anti-PD-L1-VID/eIgG1 Bispecific Antibody

Figures 14A, 14B, 14C:
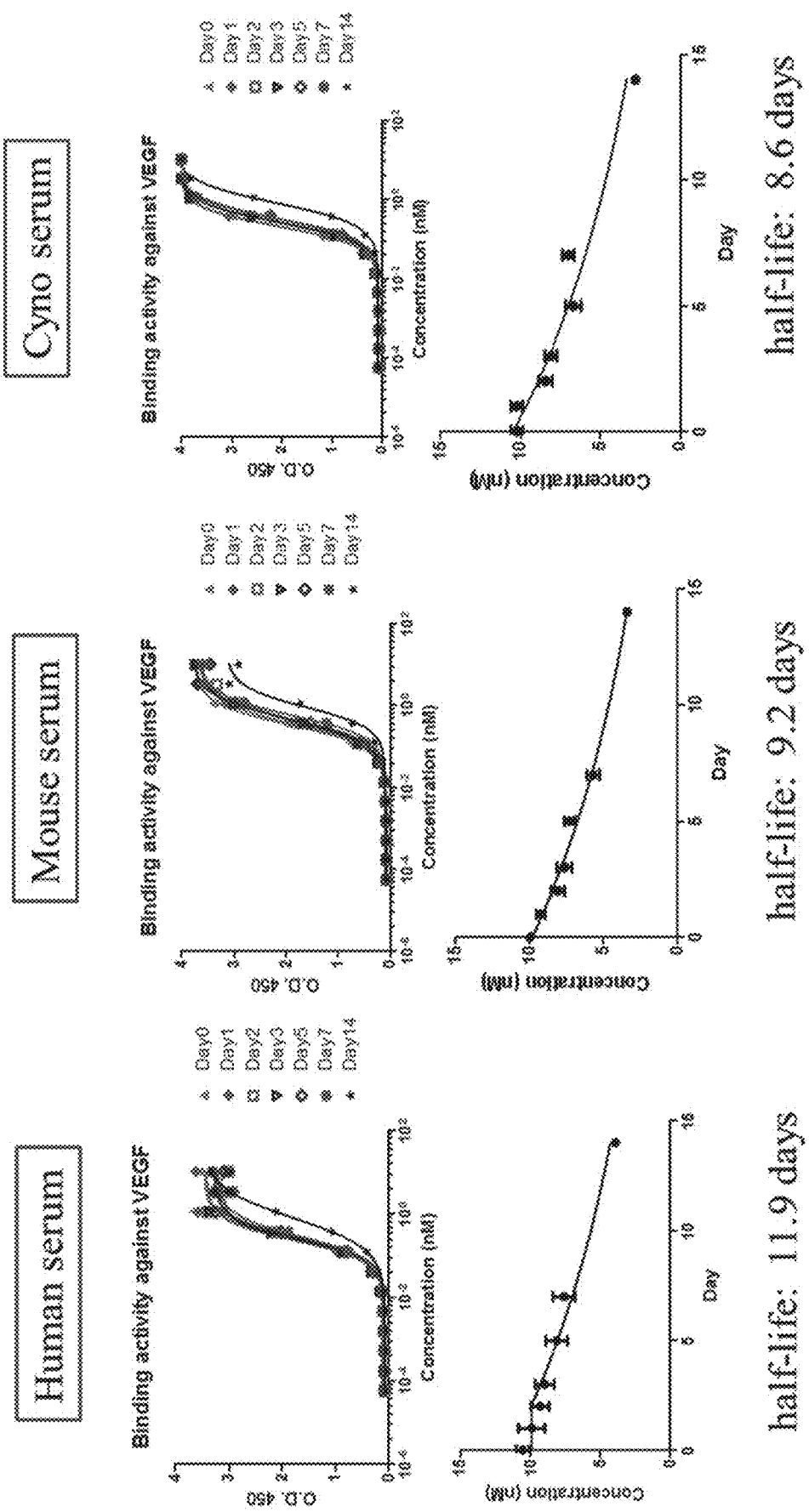
FIGS. 14A, 14B and 14C show the in vitro serum stability of anti-PD-L1-VID/eIgG1 bispecific antibody from different species (FIG. 14A: Human serum.

Purified anti-PD-L1-VID/eIgG1 were incubated with serum (15 μg/mL) from different species as indicated at 37° C. in water bath. Serum samples containing the purified bispecific antibodies were taken at different time points up to 14 days. Concentrations of the bispecific antibody in the serum samples will be determined using a sandwiched ELISA assay as below. $VEGF_{165}$ (1 μg/mL) pre-coated wells were incubated with titrated concentrations of purified anti-PD-L1-VID/eIgG1 bispecific antibody to be the standard curve to calculate the Abs concentration in the serum (fresh preparation, day 0). Collected samples from different time points were also applied to pre-coated $VEGF_{165}$ wells for detection. After washing with 0.1% Tween-20 in PBS, the intact and bound Abs were detected by biotinylated PD-L1-Fc and HRP conjugated streptavidin before color developing. The concentration of Abs in the serum was calculated by interpolation method and then the half-life of Abs is plotted as shown in the FIGS. 14A, 14B and 14C. The half-life of anti-PD-L1-VID/eIgG1 is longer than 8 days either in cynomolgus (8.6 days), mouse (9.2 days) or human serum (11.9 days). The long half-life could provide usage flexibility of the bispecific antibody with less administration frequency in animal study or clinical trial in the future.

Anti-Tumor Activity of Bispecific Antibody (In Vivo Model)

The lack of rodent cross-reactivity of the PD-L1 in bispecific antibodies prevented the use of standard murine syngeneic or human xenograft tumor models for the assessment of anti-human tumor efficacy of the antibodies. Accordingly, a novel huPBL-SCID-Bg xenogeneic tumor mouse model was generated using a SCID-Bg mouse (CB.17/Icr.Cg $Pkrd^{cscid}Lyst^{bg}$/Crl), which harbors the beige (Bg) mutation lack murine T and B lymphocytes and functional NK cells. The anti-human tumor efficacy of the bispecific antibodies was assessed using this model as described below.

The PC-3 human prostate was obtained from American Type Culture Collection and was cultured in RPMI-1640 (Invitrogen) with L-glutamine, sodium pyruvate, penicillin/streptomycin, and 10% heat-inactivated fetal bovine serum (FBS, Gibco Cat. No. 10437). Cells were grown to confluency in T-150 Falcon flasks. Subsequently, cells were trypsinized (Trypsin 0.25%-EDTA; Invitrogen) and growth was scaled up to sufficient cell number for inoculation. Peripheral blood lymphocytes (PBMCs) were isolated from heparinized blood using Lymphoprep™ in accordance with the manufactures' protocol (STEMCELL Technologies Inc.). Counted cell suspensions were combine such that each mouse received an injection of $0.75 \times 10^6$ PBMCs and $3 \times 10^6$ tumor cells in a single bolus injection of 0.1 mL in PBS. In order to facilitate the tumor cells grown in the mouse, another 0.1 mL matrigel was then mixed with the combined cell suspension and then immediately injected into prepare mice.

Figure 15A:
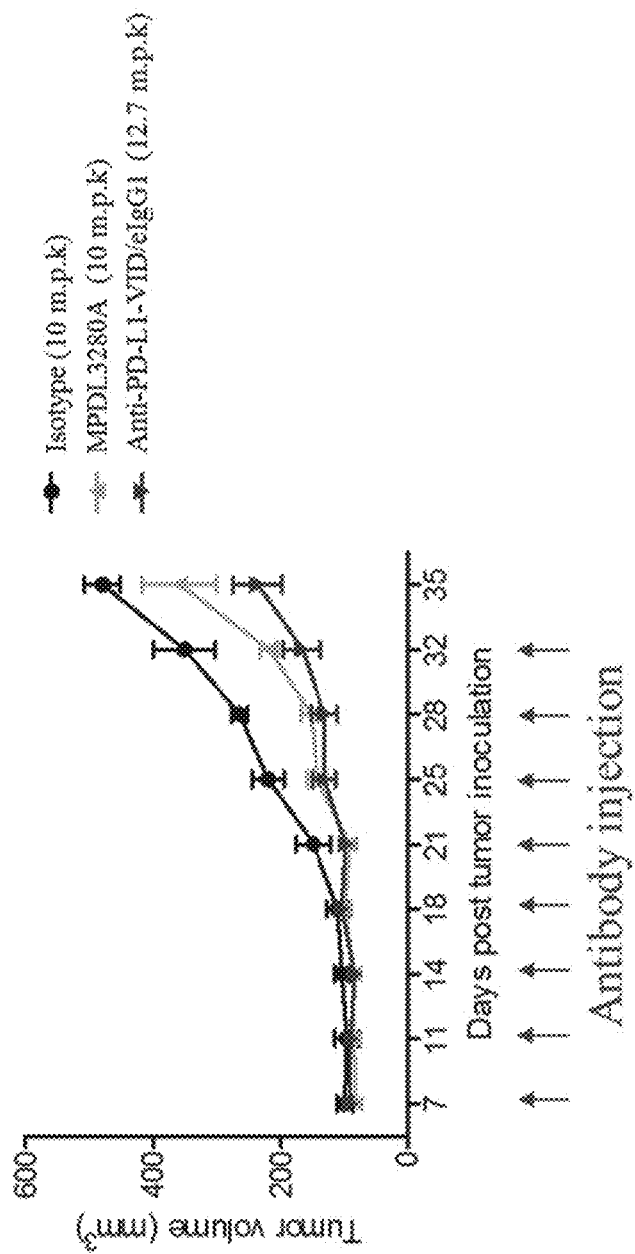
FIG. 15A is a graph showing the effect of anti-PD-L1-VID/eIgG1 bispecific antibody treatment and monoclonal antibody treatment on the growth of PC-3 tumor in Fox Chase SCID®Beige mice.
Figure 15B:
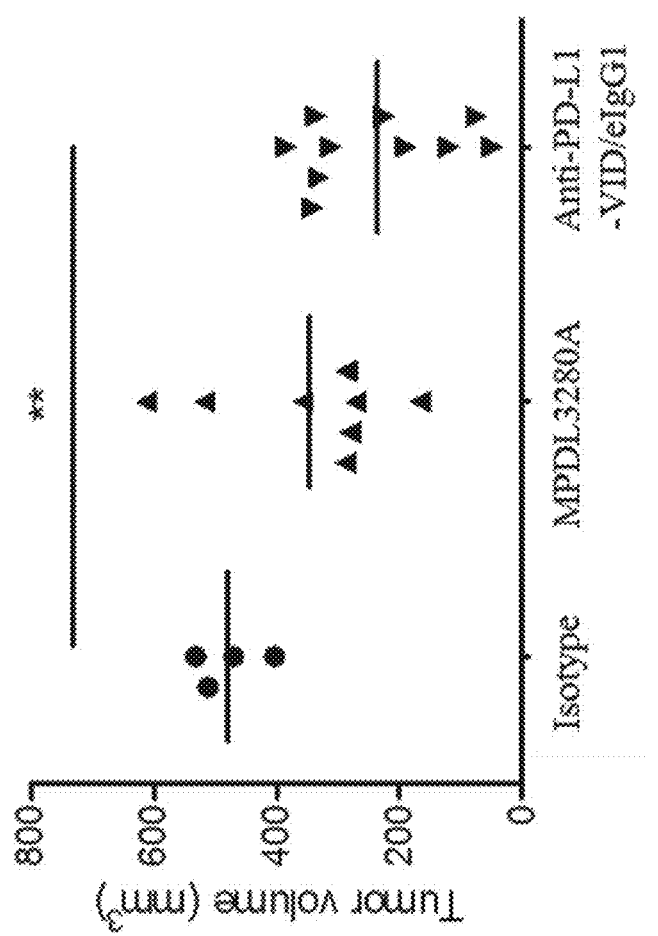
FIG. 15B shows that the tumor size bispecific antibody treatment is significant smaller than isotype or reference antibody treatment on day 35 post-inoculation.

For each mouse, 0.2 mL volume of the combined cell suspension was injected subcutaneously into the right flank of the animal. After 7 days inoculation, the solid tumor is formed and reached around ~100 $mm^3$ and the bispecific antibody (10 mg/kg) or control antibody is challenged twice per week for three to four weeks with an intraperitoneal injection (i.p.). Tumor measurement was made via Pressier caliper twice per week as well as test sample administration for the duration of the experiments and body weights were also recorded. Tumor volume was calculated using the following calculation: length×$width^2$×0.44=volume ($mm^3$) and plotted in the FIG. 15A. Mice were removed from the study in the event that the tumor volume reached 2000 $mm^3$ or animal lost 20% of body weight before termination of the experiment. Similar results were observed when tumors were measured on day 7 post-inoculation, and the animals were randomized according to tumor volume. For animal study, each group contained 6 mice. As the data showed in the FIG. 15A, the bispecific antibody showed a significant anti-tumor efficiency in the PC-3 xenografted mouse model. The tumor size is smaller after 18 days post tumor inoculation as well as PD-L1 reference antibody and continued to reduce below 200 $mm^3$. FIG. 15B shows that the tumor size bispecific antibody treatment is significant smaller than isotype or reference antibody treatment on day 35 post-inoculation. It indicated the anti-PD-L1-VID/eIgG1 Abs has the synergic effect in anti-tumor activity in animal. The PC-3 xenografted mouse model is preliminarily demonstrated the anti-tumor of bispecific antibody and revealed its potential to be a therapeutic drug lead in the future.

Collectively, these results indicated bi-specific antibody sustain its immune checkpoint blocking in PD-1/PD-L1 signaling and neutralized the pro-angiogenic protein, VEGF. Studies are ongoing to further investigate the biological activity of these proteins using proper animal model, such as the PC-3 tumor in the humanized NOD.Cg-$Prkdc^{scid}$ $Il2rg^{tm1wjl}$/SzJ (NSG) model.

The Fc region in the present invention could be from any immunoglobulin isotypes, subclasses, allotypes, or engineered mutants, such as knob and hole Fc fragment(s).

EXAMPLES

The example below describe the generation of monoclonal antibodies suitable for therapeutic purpose targeting human PD-L1 and VEGF. Composite, human anti-human PD-L1 and VEGF neutralized domains were generated from anti-PD-L1 antibody clone 6 and VEGF trapping domain from human VEGF receptors, respectively. Segments of human V region sequence were sourced from unrelated human antibody (germline and non-germline) sequence databases.

Example 1 Generation of IgG Antibodies that Bind to PD-L1 and VEGF

Certain antibodies provided by present invention were originally generated from Fabs bind to human PD-L1. The Fabs were selected from a phage display library, the Omn-iMab phagemid library, following alternating panning on corresponding Fc fusion proteins (PD-L1-Fc) and cells expressing human corresponding protein (PD-L1). After direct ELISA screening, the positive clones were then sequenced for heavy chain and light chain. These Fabs included those that are designated as "OM-PD-L1-6", and "OM-PD-L1-32" etc. for PD-L1. PD-L1 antibodies PD-L1-Clone 6, and PD-L1-Clone 32 disclosed in this application were generated from "OM-PD-L1-6" and "OM-PD-L1-32" in HEK293 cell or CHO-S cells. And bispecific antibody targeting PD-L1 and VEGF simultaneously was designed as anti-PD-L1-VID (VEGF inhibition domain) antibody. The amino acid sequence of the light chain variable region and heavy chain variable region of a given Fab are identical to the amino acid sequence of the light chain variable region and heavy chain variable region, respectively.

Example 2 In Vitro Binding of Anti-PD-L1-VID Bispecific Antibody to its Corresponding Target Anti-PD-L1-VID bispecific antibody was constructed as shown in the FIG. 8 and expressed in the HEK293 cells or CHO-S cell. The medium containing bispecific antibody was affinity purified from culture supernatant by Protein G chromatography. Purified antibody is then concentrated, followed by dialysis in PBS buffer and analyzed by SDS-PAGE as shown in the FIG. 9. To test direct binding of purified fusion proteins to PD-L1 or $VEGF_{165}$ on ELISA, 100 ng/well recombinant PD-L1 was coated in a 96-well ELISA plate. Various concentrations of purified anti-PD-L1-VID Abs were then added to each well and incubated for 1 hr. After washing, 1:5000 dilution of anti-Fab or anti-Fc HRP conjugate (Jackson Immunochemicals) was added to each well and incubated for another hour. After final washing, TMB substrate (Invitrogen Inc.) was added and OD absorbance at 450 nm was measured. The data analyzed by sigmoidal curve fitting using GraphPad Prism 5 and EC50 is calculated.

Example 3 Antigen Binding Specificity of Anti-PD-L1-VID by FACS Analysis

Figure 16A:
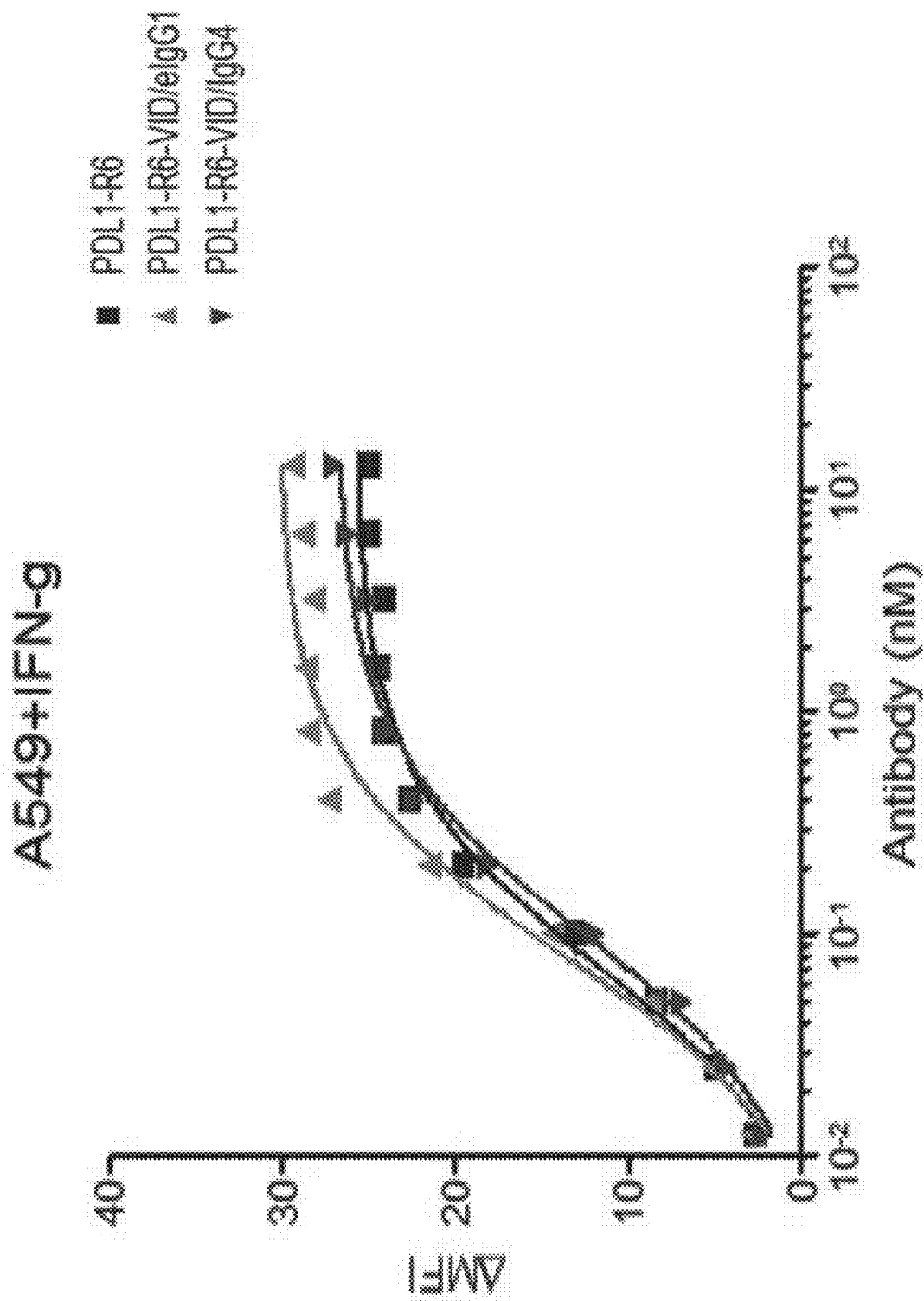
FIGS. 16A, 16B and 16C show anti-PD-L1-VID Abs sustains its antigen binding specificity as compared with anti-PD-L1 alone in IFN-γ stimulated A549 (FIG. 16A), NCI-H292 (FIG. 16B), or stable PD-L1 expression 293 cell (FIG. 16C); MFI: mean fluorescence intensity.
Figure 16B:
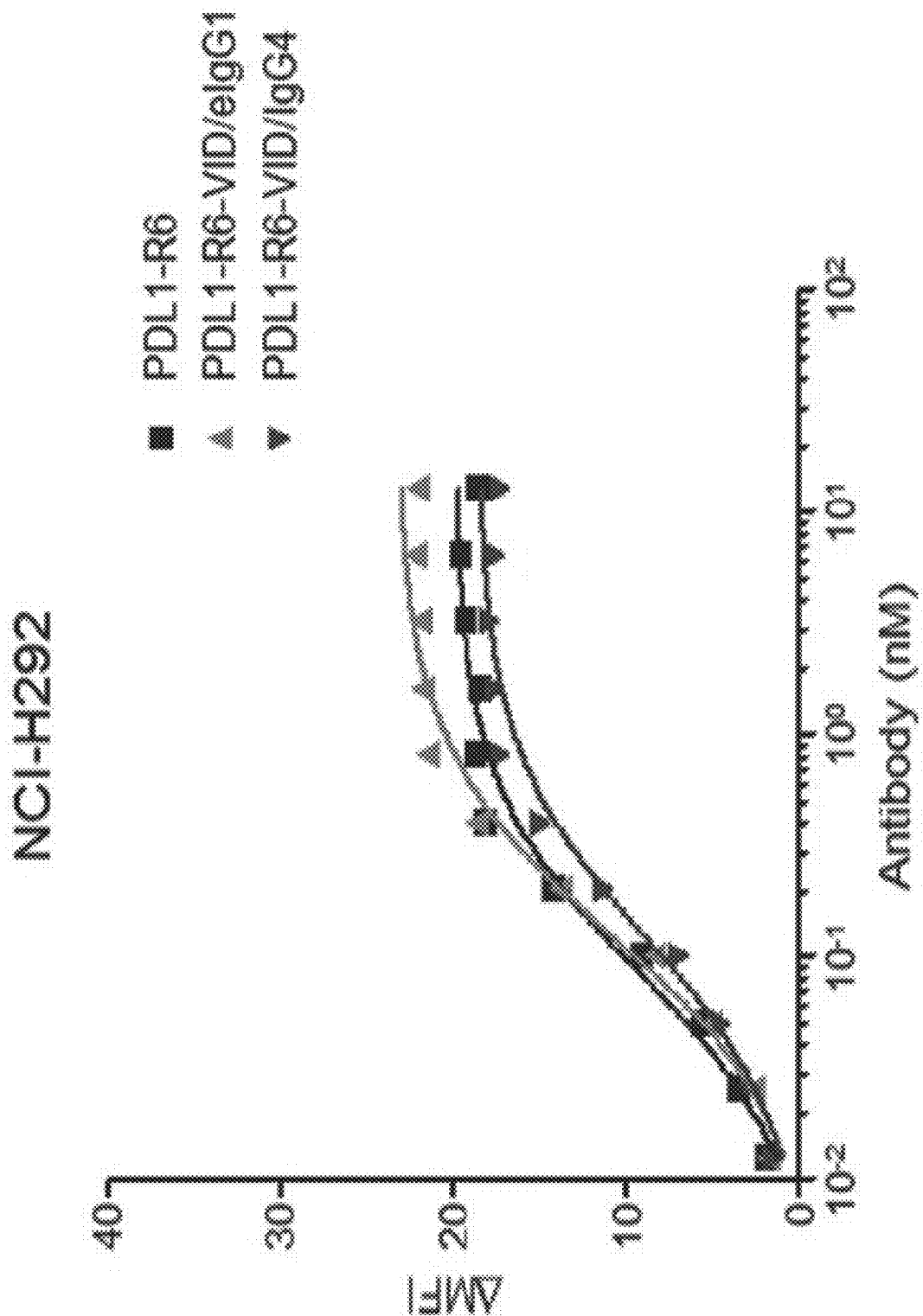
Figure 16C:
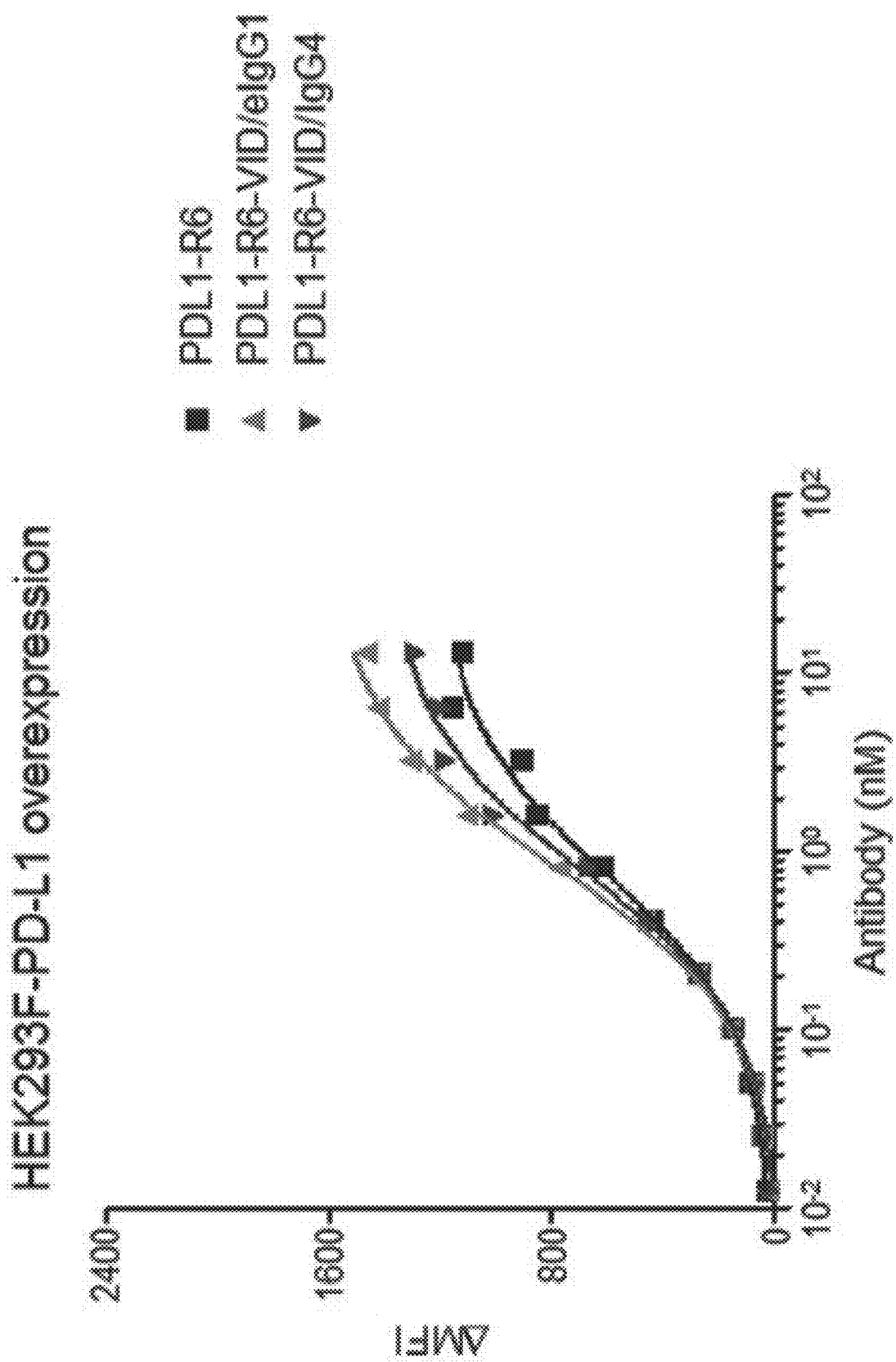

To test anti-PD-L1-VID Abs binding specificity, stable PD-L1 expression 293 cells (human embryonic kidney cells), IFN-γ stimulated A549 (lung carcinoma) or NCI-H292 (mucoepidermoid pulmonary carcinoma) were stained a 3-folds serial dilution from 30 nM with 1 μg/mL anti-PD-L1-VID Abs antibody for 1 hr on ice before wash three times with 1×PBS. The bound antibody fusion proteins were detected with Alexa-488 conjugated goat IgG (H+L) followed by FACS analysis. Isotype antibody was used as negative control for the test. Results showed anti-PD-L1-VID Abs sustains its antigen binding specificity as compared with anti-PD-L1 alone (FIGS. 16A, 16B and 16C).

Example 4 In Vitro Immunomodulatory Effect of Anti-PD-L1-VID Bi-Specific Antibody To measure the ability of the anti-PD-L1-VID Abs to modulate T cell responsiveness purified T cells will be cultured with allogeneic dendritic cells, prepared by culturing monocytes in GM-CSF and IL-4 for few days. Parallel plates were set up to allow collection of supernatants at day 3 and day 5 to measure IL-2 and IFN-γ respectively using a commercial ELISA kit. Genentech/Roche's humanized anti-PD-L1, MPDL3280A, will be produced in-house and used as positive control. As the data shown in the FIGS. 13A and 13B, the IL2 and IFN-γ production are highly upregulated in the bispecific antibody treatment as well as reference antibody after 3 or 5 days antibody treatment. It revealed the bispecific antibody still possess the ability to inhibit the PD-1/PD-L1 interaction between T cell and dendritic cells to activate the T cell activity.

Example 5 Human Leukocyte Expansion Induced by Bispecific Antibodies In Vivo The lack of detectable cross-reactivity of the PD-L1 antibody with murine PD-L1 and the requirement for the presence of human immune cells required the development of models for the in vivo functional assessment of the bispecific antibodies. Mice with the NOD genetic background carrying the severe combined immunodeficient (SCID) mutation and deficiency in the IL-2 receptor common gamma chain (commonly termed NSG) are able to support the engraftment of large number of human peripheral blood leukocytes (huPBL) and maintain engraftment for at least 30 days (King et al., 2008). This mouse model, also known as huPBL-NSG model, was used to assess the functional effect of in vivo systemic administration of the antibodies on human immune cells.

Specifically, 6 million freshly isolated human PBMCs were adoptively transferred via intravenous injection into huPBL-NSG mice. Nine days post PBMC injections, the animals were administered a single 1 mg/kg of mono-antibody, bispecific antibody or isotype control antibody via intraperitoneal injection. At day 24 to 28 post PBMC engraftment, PBMC were stained with antibodies to human and murine CD45 assessed via flow cytometry. Forward and side scatter profiles were used to determine a lymphocyte gate. Bispecific antibodies were able to enhance expansion of human leukocytes as evidenced by increased proportion of human $CD45^+$ cells in the peripheral blood of engrafted mice. For each group, n≥6 mice.

Example 6 Inhibition of PC-3 or A498 Tumor Cell Growth in huPBL-NSG by Anti-PD-L1-VID/eIgG1 Antibody PD-L1 positive human prostate cancer cell line, PC-3 (ATCC #CRL-1435) or kidney cancer cell line, A498 (ATCC® HTB-44™) can be used to establish xenograft models in huPBL-NSG mice. For tumor formation, $3 \times 10^6$ PC-3 cells (or A498 cells)/mouse will be injected subcutaneously in huPBL-NSG mice as described above. In order to assess the inhibitory effects on the tumor growth, different concentrations of anti-PD-L1-VID/eIgG1 antibody, reference antibody, or isotype antibody from 0.1-3 mg/kg will be administered intravenously twice weekly for 4 weeks in the mice after 14 days tumor cells implantation. The tumor growth will be measured twice per week up to 5 weeks as described in the Fox Chase SCID® Beige mice model.

Example 7 Pharmacokinetic Assessment of Anti-PD-L1-VID/eIgG1 in Mice and Monkeys 10 mg/kg to 40 mg/kg of bi-functional proteins, anti-PD-L1-VID/eIgG1 will be administered into mice or monkeys via subcutaneous injection or intravenous injection. Serum samples will be taken at different time points after the injection up to 15 days. Concentrations of the Fc fusion protein in the serum samples will be determined using a sandwiched ELISA assay.

While the disclosure has been described by way of example(s) and in terms of the preferred embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A fusion protein comprising an antibody or antigen-binding fragment thereof that comprises an at least one polypeptide chain, the at least one polypeptide chain comprising:
   a binding domain binding cell surface protein, wherein the binding domain binds programmed cell death protein 1 ligand (PD-L1), and the binding domain comprises:
      a heavy chain variable region comprising complementarity-determining regions (CDRs) CDR1, CDR2, and CDR3 set forth in the sequence of SEQ ID NO: 4 and a light chain variable region comprising CDR1, CDR2, and CDR3 set forth in amino acid 1-111 of SEQ ID NO: 3; and
   a vascular endothelial growth factor (VEGF) inhibiting domain comprising the amino acid sequence of SEQ ID NO: 9.

2. The fusion protein of claim 1, wherein the at least one polypeptide chain further comprises:
   an Fc domain; and
   an Fab fragment connected to the N-terminus of the Fc domain, the Fab fragment comprising the binding domain,
   wherein the VEGF inhibiting domain is connected to the C-terminus of the Fc domain.

3. The fusion protein of claim 2, further comprising a linker between the Fc domain and the VEGF inhibiting domain.

4. The fusion protein of claim 3, wherein the antibody comprises the amino acid sequence set forth in SEQ ID NO: 12 or 13.

5. The fusion protein of claim 1, wherein the antibody or antigen-binding fragment thereof comprises one or more pairs of polypeptide chains.

6. The fusion protein of claim 5, wherein the antibody is an IgG, IgE, IgM, IgD, IgA, or IgY antibody.

7. The fusion protein of claim 6, wherein the antibody is an IgG antibody.

8. The fusion protein of claim 7, wherein the IgG antibody is an IgG1, IgG2, IgG3, or IgG4 antibody.

9. The fusion protein of claim 8, wherein the IgG1 antibody is a reduction of antibody-dependent cell-mediated cytotoxity of IgG1 antibody.

10. The fusion protein of claim 1, wherein the antibody is a human antibody.

11. The fusion protein of claim 1, further comprising a therapeutic agent,
    wherein the therapeutic agent is covalently conjugated to the antibody or the antigen-binding fragment in the fusion protein by a linker.

12. The fusion protein of claim 1, wherein the heavy chain variable region comprises a sequence that is at least 90% sequence identify to the sequence of SEQ ID NO: 4, and
    wherein the light chain variable region comprises a sequence that is at least 90% sequence identify to the sequence of amino acids 1-111 of SEQ ID NO: 3, and
    wherein the at least 90% sequence identity to the amino acid sequence of SEQ ID NO: 3 or 4 excludes complementarity-determining regions (CDRs).

13. A pharmaceutical composition, comprising:
    the fusion protein of claim 1, and
    at least one pharmaceutically acceptable carrier.

14. A fusion protein comprising an antibody or antigen-binding fragment thereof that comprises an at least one polypeptide chain, the at least one polypeptide chain comprising:
    a heavy chain variable region and a light chain variable region respectively, wherein the heavy chain variable region comprises complementary-determining regions CDR1, CDR2, and CDR3 set forth in the sequence of SEQ ID NO: 4, and wherein the light chain variable region comprises complementary-determining regions CDR1, CDR2, and CDR3 set forth in amino acid 1-111 of SEQ ID NO: 3;
    a vascular endothelial growth factor (VEGF) inhibiting domain comprising the amino acid sequence of SEQ ID NO: 9.

15. The fusion protein of claim 14, wherein the heavy chain variable region comprises a sequence that is at least 90% sequence identity to the amino acid sequence of SEQ ID NO: 4,
    wherein the light chain variable region comprises a sequence that is at least 90% sequence identity to the amino acid sequence of amino acids 1-111 of SEQ ID NO: 3, and
    wherein the at least 90% sequence identity to the amino acid sequences of SEQ ID NO: 3 or 4 excludes complementarity-determining regions (CDRs).

* * * * *

UNITED STATES PATENT AND TRADEMARK OFFICE
CERTIFICATE OF CORRECTION

| | | |
|---|---|---|
| PATENT NO. | : 11,780,922 B2 | Page 1 of 1 |
| APPLICATION NO. | : 16/896597 | |
| DATED | : October 10, 2023 | |
| INVENTOR(S) | : Jeng-Horng Her et al. | |

It is certified that error appears in the above-identified patent and that said Letters Patent is hereby corrected as shown below:

On the Title Page

Column 2, Other Publication, Line 1, delete "(Protein" and insert -- Protein --

In the Claims

Column 53, Line 44, Claim 9, delete "cytotoxity" and insert -- cytotoxicity --

Column 54, Line 25, Claim 14, delete "complementary" and insert -- complementarity --

Column 54, Line 28, Claim 14, delete "complementary" and insert -- complementarity --

Column 54, Line 30, Claim 14, delete "3;" and insert -- 3; and --

Signed and Sealed this
Ninth Day of January, 2024

*Katherine Kelly Vidal*

Katherine Kelly Vidal
*Director of the United States Patent and Trademark Office*

SEQUENCE LISTING

<160> NUMBER OF SEQ ID NOS: 27

<210> SEQ ID NO 1
<211> LENGTH: 732
<212> TYPE: PRT
<213> ORGANISM: Homo sapiens

<400> SEQUENCE: 1

```
Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30

His Lys Trp Ser Leu Pro Glu Met Val Ser Lys Glu Ser Glu Arg Leu
        35                  40                  45

Ser Ile Thr Lys Ser Ala Cys Gly Arg Asn Gly Lys Gln Phe Cys Ser
    50                  55                  60

Thr Leu Thr Leu Asn Thr Ala Gln Ala Asn His Thr Gly Phe Tyr Ser
65                  70                  75                  80

Cys Lys Tyr Leu Ala Val Pro Thr Ser Lys Lys Lys Glu Thr Glu Ser
                85                  90                  95

Ala Ile Tyr Ile Phe Ile Ser Asp Thr Gly Arg Pro Phe Val Glu Met
            100                 105                 110

Tyr Ser Glu Ile Pro Glu Ile Ile His Met Thr Glu Gly Arg Glu Leu
        115                 120                 125

Val Ile Pro Cys Arg Val Thr Ser Pro Asn Ile Thr Val Thr Leu Lys
    130                 135                 140

Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Gln Ile
        195                 200                 205

Ser Thr Pro Arg Pro Val Lys Leu Leu Arg Gly His Thr Leu Val Leu
    210                 215                 220

Asn Cys Thr Ala Thr Thr Pro Leu Asn Thr Arg Val Gln Met Thr Trp
225                 230                 235                 240

Ser Tyr Pro Asp Glu Lys Asn Lys Arg Ala Ser Val Arg Arg Arg Ile
                245                 250                 255

Asp Gln Ser Asn Ser His Ala Asn Ile Phe Tyr Ser Val Leu Thr Ile
            260                 265                 270

Asp Lys Met Gln Asn Lys Asp Lys Gly Leu Tyr Thr Cys Arg Val Arg
        275                 280                 285
```

-continued

```
Ser Gly Pro Ser Phe Lys Ser Val Asn Thr Ser Val His Ile Tyr Asp
    290             295                 300
Lys Ala Phe Ile Thr Val Lys His Arg Lys Gln Gln Val Leu Glu Thr
305                 310                 315                 320
Val Ala Gly Lys Arg Ser Tyr Arg Leu Ser Met Lys Val Lys Ala Phe
                325                 330                 335
Pro Ser Pro Glu Val Val Trp Leu Lys Asp Gly Leu Pro Ala Thr Glu
                340                 345                 350
Lys Ser Ala Arg Tyr Leu Thr Arg Gly Tyr Ser Leu Ile Ile Lys Asp
                355                 360                 365
Val Thr Glu Glu Asp Ala Gly Asn Tyr Thr Ile Leu Leu Ser Ile Lys
370                 375                 380
Gln Ser Asn Val Phe Lys Asn Leu Thr Ala Thr Leu Ile Val Asn Val
385                 390                 395                 400
Lys Pro Gln Ile Tyr Glu Lys Ala Val Ser Ser Phe Pro Asp Pro Ala
                405                 410                 415
Leu Tyr Pro Leu Gly Ser Arg Gln Ile Leu Thr Cys Thr Ala Tyr Gly
                420                 425                 430
Ile Pro Gln Pro Thr Ile Lys Trp Phe Trp His Pro Cys Asn His Asn
                435                 440                 445
His Ser Glu Ala Arg Cys Asp Phe Cys Ser Asn Asn Glu Glu Ser Phe
450                 455                 460
Ile Leu Asp Ala Asp Ser Asn Met Gly Asn Arg Ile Glu Ser Ile Thr
465                 470                 475                 480
Gln Arg Met Ala Ile Ile Glu Gly Lys Asn Lys Met Ala Ser Thr Leu
                485                 490                 495
Val Val Ala Asp Ser Arg Ile Ser Gly Ile Tyr Ile Cys Ile Ala Ser
                500                 505                 510
Asn Lys Val Gly Thr Val Gly Arg Asn Ile Ser Phe Tyr Ile Thr Asp
                515                 520                 525
Val Pro Asn Gly Phe His Val Asn Leu Glu Lys Met Pro Thr Glu Gly
                530                 535                 540
Glu Asp Leu Lys Leu Ser Cys Thr Val Asn Lys Phe Leu Tyr Arg Asp
545                 550                 555                 560
Val Thr Trp Ile Leu Leu Arg Thr Val Asn Asn Arg Thr Met His Tyr
                565                 570                 575
Ser Ile Ser Lys Gln Lys Met Ala Ile Thr Lys Glu His Ser Ile Thr
                580                 585                 590
Leu Asn Leu Thr Ile Met Asn Val Ser Leu Gln Asp Ser Gly Thr Tyr
                595                 600                 605
Ala Cys Arg Ala Arg Asn Val Tyr Thr Gly Glu Glu Ile Leu Gln Lys
610                 615                 620
Lys Glu Ile Thr Ile Arg Asp Gln Glu Ala Pro Tyr Leu Leu Arg Asn
625                 630                 635                 640
Leu Ser Asp His Thr Val Ala Ile Ser Ser Ser Thr Thr Leu Asp Cys
                645                 650                 655
His Ala Asn Gly Val Pro Glu Pro Gln Ile Thr Trp Phe Lys Asn Asn
                660                 665                 670
His Lys Ile Gln Gln Glu Pro Gly Ile Ile Leu Gly Pro Gly Ser Ser
                675                 680                 685
Thr Leu Phe Ile Glu Arg Val Thr Glu Glu Asp Glu Gly Val Tyr His
                690                 695                 700
Cys Lys Ala Thr Asn Gln Lys Gly Ser Val Glu Ser Ser Ala Tyr Leu
```

```
                  705                 710                 715                 720
Thr Val Gln Gly Thr Ser Asp Lys Ser Asn Leu Glu
                725                 730

<210> SEQ ID NO 2
<211> LENGTH: 745
<212> TYPE: PRT
<213> ORGANISM: Homo sapiens

<400> SEQUENCE: 2

Ala Ser Val Gly Leu Pro Ser Val Ser Leu Asp Leu Pro Arg Leu Ser
1               5                   10                  15

Ile Gln Lys Asp Ile Leu Thr Ile Lys Ala Asn Thr Thr Leu Gln Ile
            20                  25                  30

Thr Cys Arg Gly Gln Arg Asp Leu Asp Trp Leu Trp Pro Asn Asn Gln
        35                  40                  45

Ser Gly Ser Glu Gln Arg Val Glu Val Thr Glu Cys Ser Asp Gly Leu
    50                  55                  60

Phe Cys Lys Thr Leu Thr Ile Pro Lys Val Ile Gly Asn Asp Thr Gly
65                  70                  75                  80

Ala Tyr Lys Cys Phe Tyr Arg Glu Thr Asp Leu Ala Ser Val Ile Tyr
                85                  90                  95

Val Tyr Val Gln Asp Tyr Arg Ser Pro Phe Ile Ala Ser Val Ser Asp
            100                 105                 110

Gln His Gly Val Val Tyr Ile Thr Glu Asn Lys Asn Lys Thr Val Val
        115                 120                 125

Ile Pro Cys Leu Gly Ser Ile Ser Asn Leu Asn Val Ser Leu Cys Ala
    130                 135                 140

Arg Tyr Pro Glu Lys Arg Phe Val Pro Asp Gly Asn Arg Ile Ser Trp
145                 150                 155                 160

Asp Ser Lys Lys Gly Phe Thr Ile Pro Ser Tyr Met Ile Ser Tyr Ala
                165                 170                 175

Gly Met Val Phe Cys Glu Ala Lys Ile Asn Asp Glu Ser Tyr Gln Ser
            180                 185                 190

Ile Met Tyr Ile Val Val Val Gly Tyr Arg Ile Tyr Asp Val Val
        195                 200                 205

Leu Ser Pro Ser His Gly Ile Glu Leu Ser Val Gly Glu Lys Leu Val
    210                 215                 220

Leu Asn Cys Thr Ala Arg Thr Glu Leu Asn Val Gly Ile Asp Phe Asn
225                 230                 235                 240

Trp Glu Tyr Pro Ser Ser Lys His Gln His Lys Lys Leu Val Asn Arg
                245                 250                 255

Asp Leu Lys Thr Gln Ser Gly Ser Glu Met Lys Lys Phe Leu Ser Thr
            260                 265                 270

Leu Thr Ile Asp Gly Val Thr Arg Ser Asp Gln Gly Leu Tyr Thr Cys
        275                 280                 285

Ala Ala Ser Ser Gly Leu Met Thr Lys Lys Asn Ser Thr Phe Val Arg
    290                 295                 300

Val His Glu Lys Pro Phe Val Ala Phe Gly Ser Gly Met Glu Ser Leu
305                 310                 315                 320

Val Glu Ala Thr Val Gly Glu Arg Val Arg Ile Pro Ala Lys Tyr Leu
                325                 330                 335

Gly Tyr Pro Pro Pro Glu Ile Lys Trp Tyr Lys Asn Gly Ile Pro Leu
            340                 345                 350
```

-continued

Glu Ser Asn His Thr Ile Lys Ala Gly His Val Leu Thr Ile Met Glu
            355                 360                 365
Val Ser Glu Arg Asp Thr Gly Asn Tyr Thr Val Ile Leu Thr Asn Pro
        370                 375                 380
Ile Ser Lys Glu Lys Gln Ser His Val Val Ser Leu Val Val Tyr Val
385                 390                 395                 400
Pro Pro Gln Ile Gly Glu Lys Ser Leu Ile Ser Pro Val Asp Ser Tyr
                405                 410                 415
Gln Tyr Gly Thr Thr Gln Thr Leu Thr Cys Thr Val Tyr Ala Ile Pro
            420                 425                 430
Pro Pro His His Ile His Trp Tyr Trp Gln Leu Glu Glu Cys Ala
        435                 440                 445
Asn Glu Pro Ser Gln Ala Val Ser Val Thr Asn Pro Tyr Pro Cys Glu
    450                 455                 460
Glu Trp Arg Ser Val Glu Asp Phe Gln Gly Gly Asn Lys Ile Glu Val
465                 470                 475                 480
Asn Lys Asn Gln Phe Ala Leu Ile Glu Gly Lys Asn Lys Thr Val Ser
                485                 490                 495
Thr Leu Val Ile Gln Ala Ala Asn Val Ser Ala Leu Tyr Lys Cys Glu
            500                 505                 510
Ala Val Asn Lys Val Gly Arg Gly Glu Arg Val Ile Ser Phe His Val
        515                 520                 525
Thr Arg Gly Pro Glu Ile Thr Leu Gln Pro Asp Met Gln Pro Thr Glu
    530                 535                 540
Gln Glu Ser Val Ser Leu Trp Cys Thr Ala Asp Arg Ser Thr Phe Glu
545                 550                 555                 560
Asn Leu Thr Trp Tyr Lys Leu Gly Pro Gln Pro Leu Pro Ile His Val
                565                 570                 575
Gly Glu Leu Pro Thr Pro Val Cys Lys Asn Leu Asp Thr Leu Trp Lys
            580                 585                 590
Leu Asn Ala Thr Met Phe Ser Asn Ser Thr Asn Asp Ile Leu Ile Met
        595                 600                 605
Glu Leu Lys Asn Ala Ser Leu Gln Asp Gln Gly Asp Tyr Val Cys Leu
    610                 615                 620
Ala Gln Asp Arg Lys Thr Lys Lys Arg His Cys Val Val Arg Gln Leu
625                 630                 635                 640
Thr Val Leu Glu Arg Val Ala Pro Thr Ile Thr Gly Asn Leu Glu Asn
                645                 650                 655
Gln Thr Thr Ser Ile Gly Glu Ser Ile Glu Val Ser Cys Thr Ala Ser
            660                 665                 670
Gly Asn Pro Pro Pro Gln Ile Met Trp Phe Lys Asp Asn Glu Thr Leu
        675                 680                 685
Val Glu Asp Ser Gly Ile Val Leu Lys Asp Gly Asn Arg Asn Leu Thr
    690                 695                 700
Ile Arg Arg Val Arg Lys Glu Asp Glu Gly Leu Tyr Thr Cys Gln Ala
705                 710                 715                 720
Cys Ser Val Leu Gly Cys Ala Lys Val Glu Ala Phe Phe Ile Ile Glu
                725                 730                 735
Gly Ala Gln Glu Lys Thr Asn Leu Glu
            740                 745

<210> SEQ ID NO 3
<211> LENGTH: 217
<212> TYPE: PRT

<213> ORGANISM: Homo sapiens

<400> SEQUENCE: 3

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Ala Trp Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 4
<211> LENGTH: 118
<212> TYPE: PRT
<213> ORGANISM: Homo sapiens

<400> SEQUENCE: 4

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser
        115
```

```
<210> SEQ ID NO 5
<211> LENGTH: 216
<212> TYPE: PRT
<213> ORGANISM: Homo sapiens

<400> SEQUENCE: 5

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ser Tyr
            20                  25                  30

Asn Ser Val Ser Trp Tyr Gln Gln His Pro Gly Lys Ala Pro Lys Leu
        35                  40                  45

Val Ile Tyr Glu Val Ala Asn Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 6
<211> LENGTH: 121
<212> TYPE: PRT
<213> ORGANISM: Homo sapiens

<400> SEQUENCE: 6

Gln Val Gln Leu Val Gln Ser Gly Ala Lys Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Val Pro Gly Tyr Ser Tyr Gly Pro Phe Asp Tyr Trp Gly
            100                 105                 110

Gln Gly Thr Thr Val Thr Val Ser Ser
```

```
              115                 120

<210> SEQ ID NO 7
<211> LENGTH: 328
<212> TYPE: PRT
<213> ORGANISM: Homo sapiens

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Gly Gly
                325

<210> SEQ ID NO 8
<211> LENGTH: 329
<212> TYPE: PRT
<213> ORGANISM: Artificial Sequence
<220> FEATURE:
```

<223> OTHER INFORMATION: constant domain in heavy chain of engineered
      IgG1 (eIgG1)

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 9
<211> LENGTH: 205
<212> TYPE: PRT
<213> ORGANISM: Homo sapiens

<400> SEQUENCE: 9

Gly Asp Thr Gly Arg Pro Phe Val Glu Met Tyr Ser Glu Ile Pro Glu
1               5                   10                  15

```
Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
 50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
            195                 200                 205

<210> SEQ ID NO 10
<211> LENGTH: 15
<212> TYPE: PRT
<213> ORGANISM: Artificial Sequence
<220> FEATURE:
<223> OTHER INFORMATION: peptide linker

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 20
<212> TYPE: PRT
<213> ORGANISM: Artificial Sequence
<220> FEATURE:
<223> OTHER INFORMATION: signal peptide

<400> SEQUENCE: 11

Met Glu Thr Asp Thr Leu Leu Leu Trp Val Leu Leu Leu Trp Val Pro
1               5                   10                  15

Gly Ser Thr Gly
            20

<210> SEQ ID NO 12
<211> LENGTH: 666
<212> TYPE: PRT
<213> ORGANISM: Artificial Sequence
<220> FEATURE:
<223> OTHER INFORMATION: Anti-PD-L1-clone 6 Heavy Chain -VID/IgG4
      bispecific antibody

<400> SEQUENCE: 12

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
```

```
            435                 440                 445
Gly Gly Ser Gly Gly Gly Ser Gly Gly Gly Ser Gly Asp Thr
    450                 455                 460

Gly Arg Pro Phe Val Glu Met Tyr Ser Glu Ile Pro Glu Ile Ile His
465                 470                 475                 480

Met Thr Glu Gly Arg Glu Leu Val Ile Pro Cys Arg Val Thr Ser Pro
                485                 490                 495

Asn Ile Thr Val Thr Leu Lys Lys Phe Pro Leu Asp Thr Leu Ile Pro
            500                 505                 510

Asp Gly Lys Arg Ile Ile Trp Asp Ser Arg Lys Gly Phe Ile Ile Ser
        515                 520                 525

Asn Ala Thr Tyr Lys Glu Ile Gly Leu Leu Thr Cys Glu Ala Thr Val
530                 535                 540

Asn Gly His Leu Tyr Lys Thr Asn Tyr Leu Thr His Arg Gln Thr Asn
545                 550                 555                 560

Thr Ile Ile Asp Val Val Leu Ser Pro Ser His Gly Ile Glu Leu Ser
                565                 570                 575

Val Gly Glu Lys Leu Val Leu Asn Cys Thr Ala Arg Thr Glu Leu Asn
            580                 585                 590

Val Gly Ile Asp Phe Asn Trp Glu Tyr Pro Ser Ser Lys His Gln His
        595                 600                 605

Lys Lys Leu Val Asn Arg Asp Leu Lys Thr Gln Ser Gly Ser Glu Met
610                 615                 620

Lys Lys Phe Leu Ser Thr Leu Thr Ile Asp Gly Val Thr Arg Ser Asp
625                 630                 635                 640

Gln Gly Leu Tyr Thr Cys Ala Ala Ser Ser Gly Leu Met Thr Lys Lys
                645                 650                 655

Asn Ser Thr Phe Val Arg Val His Glu Lys
            660                 665

<210> SEQ ID NO 13
<211> LENGTH: 669
<212> TYPE: PRT
<213> ORGANISM: Artificial Sequence
<220> FEATURE:
<223> OTHER INFORMATION: Anti-PD-L1-clone 6 Heavy Chain -VID/eIgG1
      bispecific antibody

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125
```

```
Leu Ala Pro Ser Ser Lys Ser Thr Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
            435                 440                 445

Gly Gly Gly Gly Gly Ser Gly Gly Gly Gly Ser Gly Gly Gly Gly Ser
450                 455                 460

Gly Asp Thr Gly Arg Pro Phe Val Glu Met Tyr Ser Glu Ile Pro Glu
465                 470                 475                 480

Ile Ile His Met Thr Glu Gly Arg Glu Leu Val Ile Pro Cys Arg Val
                485                 490                 495

Thr Ser Pro Asn Ile Thr Val Thr Leu Lys Lys Phe Pro Leu Asp Thr
            500                 505                 510

Leu Ile Pro Asp Gly Lys Arg Ile Ile Trp Asp Ser Arg Lys Gly Phe
            515                 520                 525

Ile Ile Ser Asn Ala Thr Tyr Lys Glu Ile Gly Leu Leu Thr Cys Glu
            530                 535                 540

Ala Thr Val Asn Gly His Leu Tyr Lys Thr Asn Tyr Leu Thr His Arg
```

```
545                 550                 555                 560
Gln Thr Asn Thr Ile Ile Asp Val Val Leu Ser Pro Ser His Gly Ile
                565                 570                 575
Glu Leu Ser Val Gly Glu Lys Leu Val Leu Asn Cys Thr Ala Arg Thr
                580                 585                 590
Glu Leu Asn Val Gly Ile Asp Phe Asn Trp Glu Tyr Pro Ser Ser Lys
                595                 600                 605
His Gln His Lys Lys Leu Val Asn Arg Asp Leu Lys Thr Gln Ser Gly
                610                 615                 620
Ser Glu Met Lys Lys Phe Leu Ser Thr Leu Thr Ile Asp Gly Val Thr
625                 630                 635                 640
Arg Ser Asp Gln Gly Leu Tyr Thr Cys Ala Ala Ser Ser Gly Leu Met
                645                 650                 655
Thr Lys Lys Asn Ser Thr Phe Val Arg Val His Glu Lys
                660                 665
```

<210> SEQ ID NO 14
<211> LENGTH: 49
<212> TYPE: PRT
<213> ORGANISM: Homo sapiens

<400> SEQUENCE: 14

```
Pro Glu Leu Ser Leu Lys Gly Thr Gln His Ile Met Gln Ala Gly Gln
1               5                   10                  15
Thr Leu His Leu Gln Cys Arg Gly Glu Ala Ala His Lys Trp Ser Leu
                20                  25                  30
Pro Glu Met Val Ser Lys Glu Ser Glu Arg Leu Ser Ile Thr Lys Ser
                35                  40                  45
Ala
```

<210> SEQ ID NO 15
<211> LENGTH: 64
<212> TYPE: PRT
<213> ORGANISM: Homo sapiens

<400> SEQUENCE: 15

```
Gly Arg Glu Leu Val Ile Pro Cys Arg Val Thr Ser Pro Asn Ile Thr
1               5                   10                  15
Val Thr Leu Lys Lys Phe Pro Leu Asp Thr Leu Ile Pro Asp Gly Lys
                20                  25                  30
Arg Ile Ile Trp Asp Ser Arg Lys Gly Phe Ile Ile Ser Asn Ala Thr
                35                  40                  45
Tyr Lys Glu Ile Gly Leu Leu Thr Cys Glu Ala Thr Val Asn Gly His
                50                  55                  60
```

<210> SEQ ID NO 16
<211> LENGTH: 98
<212> TYPE: PRT
<213> ORGANISM: Homo sapiens

<400> SEQUENCE: 16

```
Ile Asp Val Gln Ile Ser Thr Pro Arg Pro Val Lys Leu Leu Arg Gly
1               5                   10                  15
His Thr Leu Val Leu Asn Cys Thr Ala Thr Thr Pro Leu Asn Thr Arg
                20                  25                  30
Val Gln Met Thr Trp Ser Tyr Pro Asp Glu Lys Asn Lys Arg Ala Ser
                35                  40                  45
```

Val Arg Arg Ile Asp Gln Ser Asn Ser His Ala Asn Ile Phe Tyr
 50                  55                  60

Ser Val Leu Thr Ile Asp Lys Met Gln Asn Lys Asp Lys Gly Leu Tyr
 65                  70                  75                  80

Thr Cys Arg Val Arg Ser Gly Pro Ser Phe Lys Ser Val Asn Thr Ser
                 85                  90                  95

Val His

<210> SEQ ID NO 17
<211> LENGTH: 87
<212> TYPE: PRT
<213> ORGANISM: Homo sapiens

<400> SEQUENCE: 17

Thr Val Lys His Arg Lys Gln Gln Val Leu Glu Thr Val Ala Gly Lys
 1               5                  10                  15

Arg Ser Tyr Arg Leu Ser Met Lys Val Lys Ala Phe Pro Ser Pro Glu
                 20                  25                  30

Val Val Trp Leu Lys Asp Gly Leu Pro Ala Thr Glu Lys Ser Ala Arg
             35                  40                  45

Tyr Leu Thr Arg Gly Tyr Ser Leu Ile Ile Lys Asp Val Thr Glu Glu
 50                  55                  60

Asp Ala Gly Asn Tyr Thr Ile Leu Leu Ser Ile Lys Gln Ser Asn Val
 65                  70                  75                  80

Phe Lys Asn Leu Thr Ala Thr
                 85

<210> SEQ ID NO 18
<211> LENGTH: 126
<212> TYPE: PRT
<213> ORGANISM: Homo sapiens

<400> SEQUENCE: 18

Pro Gln Ile Tyr Glu Lys Ala Val Ser Ser Phe Pro Asp Pro Ala Leu
 1               5                  10                  15

Tyr Pro Leu Gly Ser Arg Gln Ile Leu Thr Cys Thr Ala Tyr Gly Ile
                 20                  25                  30

Pro Gln Pro Thr Ile Lys Trp Phe Trp His Pro Cys Asn His Asn His
             35                  40                  45

Ser Glu Ala Arg Cys Asp Phe Cys Ser Asn Asn Glu Glu Ser Phe Ile
 50                  55                  60

Leu Asp Ala Asp Ser Asn Met Gly Asn Arg Ile Glu Ser Ile Thr Gln
 65                  70                  75                  80

Arg Met Ala Ile Ile Glu Gly Lys Asn Lys Met Ala Ser Thr Leu Val
                 85                  90                  95

Val Ala Asp Ser Arg Ile Ser Gly Ile Tyr Ile Cys Ile Ala Ser Asn
             100                 105                 110

Lys Val Gly Thr Val Gly Arg Asn Ile Ser Phe Tyr Ile Thr
 115                 120                 125

<210> SEQ ID NO 19
<211> LENGTH: 94
<212> TYPE: PRT
<213> ORGANISM: Homo sapiens

<400> SEQUENCE: 19

Pro Asn Gly Phe His Val Asn Leu Glu Lys Met Pro Thr Glu Gly Glu
 1               5                  10                  15

```
Asp Leu Lys Leu Ser Cys Thr Val Asn Lys Phe Leu Tyr Arg Asp Val
            20                  25                  30

Thr Trp Ile Leu Leu Arg Thr Val Asn Asn Arg Thr Met His Tyr Ser
        35                  40                  45

Ile Ser Lys Gln Lys Met Ala Ile Thr Lys Glu His Ser Ile Thr Leu
 50                  55                  60

Asn Leu Thr Ile Met Asn Val Ser Leu Gln Asp Ser Gly Thr Tyr Ala
 65                  70                  75                  80

Cys Arg Ala Arg Asn Val Tyr Thr Gly Glu Glu Ile Leu Gln
                85                  90

<210> SEQ ID NO 20
<211> LENGTH: 87
<212> TYPE: PRT
<213> ORGANISM: Homo sapiens

<400> SEQUENCE: 20

Pro Tyr Leu Leu Arg Asn Leu Ser Asp His Thr Val Ala Ile Ser Ser
 1               5                  10                  15

Ser Thr Thr Leu Asp Cys His Ala Asn Gly Val Pro Glu Pro Gln Ile
            20                  25                  30

Thr Trp Phe Lys Asn Asn His Lys Ile Gln Gln Glu Pro Gly Ile Ile
        35                  40                  45

Leu Gly Pro Gly Ser Ser Thr Leu Phe Ile Glu Arg Val Thr Glu Glu
 50                  55                  60

Asp Glu Gly Val Tyr His Cys Lys Ala Thr Asn Gln Lys Gly Ser Val
 65                  70                  75                  80

Glu Ser Ser Ala Tyr Leu Thr
                85

<210> SEQ ID NO 21
<211> LENGTH: 65
<212> TYPE: PRT
<213> ORGANISM: Homo sapiens

<400> SEQUENCE: 21

Asn Thr Thr Leu Gln Ile Thr Cys Arg Gly Gln Arg Asp Leu Asp Trp
 1               5                  10                  15

Leu Trp Pro Asn Asn Gln Ser Gly Ser Glu Gln Arg Val Glu Val Thr
            20                  25                  30

Glu Cys Ser Asp Gly Leu Phe Cys Lys Thr Leu Thr Ile Pro Lys Val
        35                  40                  45

Ile Gly Asn Asp Thr Gly Ala Tyr Lys Cys Phe Tyr Arg Glu Thr Asp
 50                  55                  60

Leu
 65

<210> SEQ ID NO 22
<211> LENGTH: 67
<212> TYPE: PRT
<213> ORGANISM: Homo sapiens

<400> SEQUENCE: 22

Asn Lys Asn Lys Thr Val Val Ile Pro Cys Leu Gly Ser Ile Ser Asn
 1               5                  10                  15

Leu Asn Val Ser Leu Cys Ala Arg Tyr Pro Glu Lys Arg Phe Val Pro
            20                  25                  30
```

```
Asp Gly Asn Arg Ile Ser Trp Asp Ser Lys Lys Gly Phe Thr Ile Pro
            35                  40                  45

Ser Tyr Met Ile Ser Tyr Ala Gly Met Val Phe Cys Glu Ala Lys Ile
    50                  55                  60

Asn Asp Glu
65

<210> SEQ ID NO 23
<211> LENGTH: 97
<212> TYPE: PRT
<213> ORGANISM: Homo sapiens

<400> SEQUENCE: 23

Tyr Asp Val Val Leu Ser Pro Ser His Gly Ile Glu Leu Ser Val Gly
1               5                   10                  15

Glu Lys Leu Val Leu Asn Cys Thr Ala Arg Thr Glu Leu Asn Val Gly
            20                  25                  30

Ile Asp Phe Asn Trp Glu Tyr Pro Ser Ser Lys His Gln His Lys Lys
            35                  40                  45

Leu Val Asn Arg Asp Leu Lys Thr Gln Ser Gly Ser Glu Met Lys Lys
    50                  55                  60

Phe Leu Ser Thr Leu Thr Ile Asp Gly Val Thr Arg Ser Asp Gln Gly
65                  70                  75                  80

Leu Tyr Thr Cys Ala Ala Ser Ser Gly Leu Met Thr Lys Lys Asn Ser
                85                  90                  95

Thr

<210> SEQ ID NO 24
<211> LENGTH: 86
<212> TYPE: PRT
<213> ORGANISM: Homo sapiens

<400> SEQUENCE: 24

Phe Val Ala Phe Gly Ser Gly Met Glu Ser Leu Val Glu Ala Thr Val
1               5                   10                  15

Gly Glu Arg Val Arg Ile Pro Ala Lys Tyr Leu Gly Tyr Pro Pro Pro
            20                  25                  30

Glu Ile Lys Trp Tyr Lys Asn Gly Ile Pro Leu Glu Ser Asn His Thr
            35                  40                  45

Ile Lys Ala Gly His Val Leu Thr Ile Met Glu Val Ser Glu Arg Asp
    50                  55                  60

Thr Gly Asn Tyr Thr Val Ile Leu Thr Asn Pro Ile Ser Lys Glu Lys
65                  70                  75                  80

Gln Ser His Val Val Ser
                85

<210> SEQ ID NO 25
<211> LENGTH: 128
<212> TYPE: PRT
<213> ORGANISM: Homo sapiens

<400> SEQUENCE: 25

Pro Gln Ile Gly Glu Lys Ser Leu Ile Ser Pro Val Asp Ser Tyr Gln
1               5                   10                  15

Tyr Gly Thr Thr Gln Thr Leu Thr Cys Thr Val Tyr Ala Ile Pro Pro
            20                  25                  30

Pro His His Ile His Trp Tyr Trp Gln Leu Glu Glu Glu Cys Ala Asn
            35                  40                  45
```

```
Glu Pro Ser Gln Ala Val Ser Val Thr Asn Pro Tyr Pro Cys Glu Glu
         50                  55                  60

Trp Arg Ser Val Glu Asp Phe Gln Gly Gly Asn Lys Ile Glu Val Asn
 65                  70                  75                  80

Lys Asn Gln Phe Ala Leu Ile Glu Gly Lys Asn Lys Thr Val Ser Thr
                 85                  90                  95

Leu Val Ile Gln Ala Ala Asn Val Ser Ala Leu Tyr Lys Cys Glu Ala
            100                 105                 110

Val Asn Lys Val Gly Arg Gly Glu Arg Val Ile Ser Phe His Val Thr
            115                 120                 125

<210> SEQ ID NO 26
<211> LENGTH: 110
<212> TYPE: PRT
<213> ORGANISM: Homo sapiens

<400> SEQUENCE: 26

Pro Glu Ile Thr Leu Gln Pro Asp Met Gln Pro Thr Glu Gln Glu Ser
 1               5                  10                  15

Val Ser Leu Trp Cys Thr Ala Asp Arg Ser Thr Phe Glu Asn Leu Thr
                20                  25                  30

Trp Tyr Lys Leu Gly Pro Gln Pro Leu Pro Ile His Val Gly Glu Leu
             35                  40                  45

Pro Thr Pro Val Cys Lys Asn Leu Asp Thr Leu Trp Lys Leu Asn Ala
 50                  55                  60

Thr Met Phe Ser Asn Ser Thr Asn Asp Ile Leu Ile Met Glu Leu Lys
 65                  70                  75                  80

Asn Ala Ser Leu Gln Asp Gln Gly Asp Tyr Val Cys Leu Ala Gln Asp
                 85                  90                  95

Arg Lys Thr Lys Lys Arg His Cys Val Val Arg Gln Leu Thr
            100                 105                 110

<210> SEQ ID NO 27
<211> LENGTH: 87
<212> TYPE: PRT
<213> ORGANISM: Homo sapiens

<400> SEQUENCE: 27

Pro Thr Ile Thr Gly Asn Leu Glu Asn Gln Thr Thr Ser Ile Gly Glu
 1               5                  10                  15

Ser Ile Glu Val Ser Cys Thr Ala Ser Gly Asn Pro Pro Pro Gln Ile
                20                  25                  30

Met Trp Phe Lys Asp Asn Glu Thr Leu Val Glu Asp Ser Gly Ile Val
             35                  40                  45

Leu Lys Asp Gly Asn Arg Asn Leu Thr Ile Arg Arg Val Arg Lys Glu
 50                  55                  60

Asp Glu Gly Leu Tyr Thr Cys Gln Ala Cys Ser Val Leu Gly Cys Ala
 65                  70                  75                  80

Lys Val Glu Ala Phe Phe Ile
                 85
```